(12) United States Patent
Szewczyk et al.

(10) Patent No.: US 7,442,693 B2
(45) Date of Patent: Oct. 28, 2008

(54) DIAZEPINE COMPOUNDS AS LIGANDS OF THE MELANOCORTIN 1 AND/OR 4 RECEPTORS

(75) Inventors: Jerzy Ryszard Szewczyk, Durham, NC (US); Jason Daniel Speake, Durham, NC (US); Douglas McCord Sammond, Carrboro, NC (US); Ronald George Sherrill, Durham, NC (US)

(73) Assignee: SmithKline Beecham Corporation, Philadephia, PA (US)

( * ) Notice: Subject to any disclaimer, the term of this patent is extended or adjusted under 35 U.S.C. 154(b) by 35 days.

(21) Appl. No.: 11/569,257

(22) PCT Filed: May 27, 2005

(86) PCT No.: PCT/US2005/018773

§ 371 (c)(1),
(2), (4) Date: Nov. 17, 2006

(87) PCT Pub. No.: WO2005/118573

PCT Pub. Date: Dec. 15, 2005

(65) Prior Publication Data

US 2007/0270411 A1    Nov. 22, 2007

Related U.S. Application Data

(60) Provisional application No. 60/575,644, filed on May 28, 2004.

(51) Int. Cl.
  C07D 401/14  (2006.01)
  C07D 403/06  (2006.01)
  C07D 403/14  (2006.01)
  A61K 31/551  (2006.01)
  A61P 3/04    (2006.01)
(52) U.S. Cl. .................... 514/218; 540/492
(58) Field of Classification Search ........... 540/492; 514/218
  See application file for complete search history.

(56) References Cited

U.S. PATENT DOCUMENTS

2003/0220324 A1    11/2003    Fotsch et al.

FOREIGN PATENT DOCUMENTS

| WO | WO95/28391 | 10/1995 |
| WO | WO96/11940 | 4/1996 |
| WO | WO00/33658 | 6/2000 |
| WO | WO02/070511 | 9/2002 |

OTHER PUBLICATIONS

Tyle, Iontophoretic Devices for Drug Delivery, Pharm. Res. 3(6):318-326 (1986).

*Primary Examiner*—Bruck Kifle
(74) *Attorney, Agent, or Firm*—Bonnie L. Deppenbrock

(57) ABSTRACT

There is provided novel diazepines that function as agonists at the melanocortin 4 receptor and as agonists at the melanocortin 1 receptor, pharmaceutical compositions containing them, methods for their use in treatment, and processes for their preparation.

3 Claims, No Drawings

DIAZEPINE COMPOUNDS AS LIGANDS OF THE MELANOCORTIN 1 AND/OR 4 RECEPTORS

CROSS-REFERENCE TO RELATED APPLICATIONS

This application is filed pursuant to 35 USC 371 as a United States National Phase Application of International Patent Application Serial No. PCT/US2005/018773 filed on May 27, 2005, which claims priority from 60/575,644 filed on May 28, 2004 in the United States.

FIELD OF THE INVENTION

This invention relates to diazepine derivatives which function as agonists at the melanocortin 4 receptor (MC4R) and/or as agonists at the melanocortin 1 receptor (MC1R), to pharmaceutical compositions containing them, to processes for their preparation, and to their use in the treatment of diseases or conditions mediated by melanocortin 4 receptor (MC4R) and/or melanocortin 1 receptor (MC1R) including obesity, pain and inflammation.

BACKGROUND OF THE INVENTION

Obesity is a medical condition that is reaching epidemic proportions among humans in a number of countries throughout the world. It is a condition that is also associated with or induces other diseases or conditions that disrupt life's activities and lifestyles. Obesity is recognized as a serious risk factor for other diseases and conditions such as diabetes, hypertension, and arteriosclerosis and can contribute to elevated levels of cholesterol in the blood. It is also recognised that increased body weight due to obesity can place a burden on joints, such as knee joints, causing arthritis, pain, and stiffness. Obesity can contribute to certain skin conditions such as atopic dermatitis and bed sores. Because overeating and obesity have become such a problem in the general population, many individuals are now interested in losing weight, reducing weight, and/or maintaining a healthy body weight and lifestyle.

Pro-opiomelanocortin (POMC) derived peptides are known to affect food intake. Several lines of evidence support the idea that the G-protein coupled receptors (GPCRs) of the melanocortin receptor (MC-R) family, several of which are expressed in the brain, are targets of POMC derived peptides involved in the control of food intake and/or metabolism.

A specific, single MC-R targeted for the control of obesity has not yet been identified. To date five distinct MC-R's have been identified, and these are expressed in different tissues. MC-1R is mainly expressed in melanocytes. MC-2R is expressed in the adrenal gland. MC-3R is expressed in the brain, gut, and placenta and may be involved in the control of food intake and thermogenesis. MC-4R is uniquely expressed in the brain, and its inactivation was shown to cause obesity. Evidence has been presented that MC-4R signaling is important in mediating feed behavior. MC-5R is expressed in many tissues, including white fat, placenta, and exocrine glands. A low level of expression of MC-5R is also observed in the brain.

WO 00/33658 discloses methods and compositions for treating a variety of disorders associated with or caused by undesirable body weight, including obesity as well as "wasting disorders".

WO 96/11940 discloses acyl amino acetamide derivatives with agonist activity for CCK-A receptors.

There is an on-going need for the development of a melanocortin-4 agonist useful in the treatment of obesity and other associated diseases and conditions. There is still further a need for a melanocortin-1 agonist useful in the treatment of inflammation and pain.

Accordingly, there is provided a novel group of diazepines that exhibit a useful profile of activity as agonists of the melanocortin-4 receptor and/or melanocortin-1 receptor (i.e., preferably they have MC4R and MC1R agonist activity). Novel compounds of the invention are useful in the treatment of obesity and other associated diseases and conditions.

The compounds of the invention serving as MC-1R agonists provide one or more of the following: (1) activate MC1-receptors selectively and with high potency, (2) antagonize the action of other hormones and agonists on the MC1-receptors selectively and with high potency, and/or (3) provide a method for administration of such compounds to animals, including humans. Novel compounds of the invention are disclosed showing high selectivity and high affinity for MC1-receptors in combination with effective stimulation of cAMP formation in MC1-receptor expressing cells. These compounds of the invention show low or negligible affinity for other subtypes of MC-receptors. The present invention discloses novel compounds which inhibit the production of nitric oxide (NO). Such novel diazepine compounds of the invention are melanocortin-1 agonist compounds and are thus also useful in the treatment of inflammation and pain.

SUMMARY OF THE INVENTION

The present invention provides a compound of Formula 1:

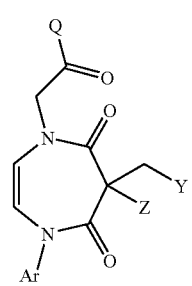

(Formula 1)

or a pharmaceutically acceptable salt, solvate, or physiologically functional derivative thereof, wherein:

Ar is aryl or heteroaryl having 5-14 ring members, each of which may be optionally substituted by one to four substituents each of which is independently selected from $C_{1-6}$alkyl, $C_{1-6}$alkenyl, halo, amino, $C_{1-6}$alkylamino, $C_{1-6}$dialkylamino, hydroxy, $C_{1-6}$alkoxy, $C_{1-6}$haloalkoxy, $C_{1-6}$haloalkyl, cyano or $C_{1-6}$alkylsulfanyl;

Q is

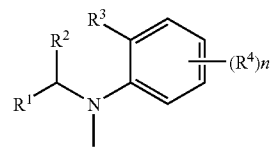

wherein $R^1$, $R^2$ and $R^4$ independently represent H, OH, halo, $C_{1-6}$alkyl, $C_{1-6}$alkoxy, $C_{1-6}$haloalkyl, $C_{1-6}$haloalkoxy, $NH_2$, $C_{1-6}$alkylamino;

n=0, 1 or 2;

R³ is H or, together with R² forms a 6 or 7 membered ring.

Y is selected from the group consisting of

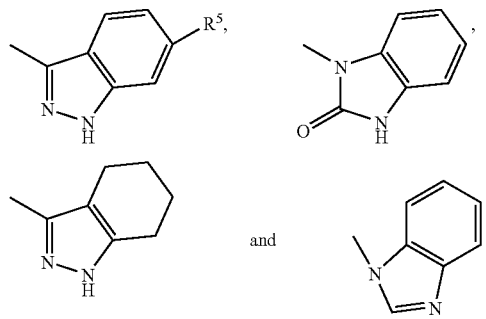

wherein R⁵ is selected from H and F; and

Z is selected from hydrogen and $C_1$-$C_6$ alkoxy;

with the proviso that the compound is not 2-[6-1H-indazol-3-ylmethyl)-5,7-dioxo-4-phenyl-4,5,6,7-tetrahydro-1H-1,4-diazepin-1-yl]-N-isopropyl-N-(4-methoxyphenyl)acetamide.

In a second aspect there is provided a compound of formula 1, a physiologically acceptable salt, solvate, or physiologically functional derivative thereof for use in therapy.

In another aspect of the invention, there is provided a pharmaceutical composition comprising a compound of Formula 1, a physiologically acceptable salt, solvate, or physiologically functional derivative thereof and one or more pharmaceutically acceptable carriers; dilutents and excipients.

In a fourth aspect of the present invention, there is provided a method of treating a disorder in a mammal, said disorder being mediated by MC4R and/or MC1R, comprising: administering to said mammal a therapeutically effective amount of a compound of formula (Ia).

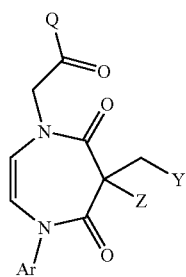

(Formula 1a)

or a pharmaceutically acceptable salt, solvate, or physiologically functional derivative thereof, wherein:

Ar is aryl or heteroaryl having 5-14 ring members, each of which may be optionally substituted by one to four substituents each of which is independently selected from $C_{1-6}$alkyl, $C_{1-6}$alkenyl, halo, amino, $C_{1-6}$alkylamino, $C_{1-6}$dialkylamino, hydroxy, $C_{1-6}$alkoxy, $C_{1-6}$haloalkoxy, $C_{1-6}$haloalkyl, cyano or $C_{1-6}$alkylsulfanyl;

Q is

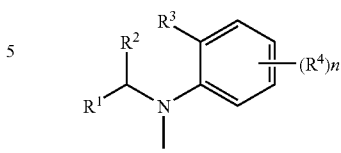

wherein R¹, R² and R⁴ independently represent H, OH, halo, $C_{1-6}$alkyl,
$C_{1-6}$alkoxy,
$C_{1-6}$haloalkyl, $C_{1-6}$haloalkoxy, $NH_2$, $C_{1-6}$alkylamino;

n=0, 1 or 2;

R³ is H or, together with R² forms a 6 or 7 membered ring;

Y is selected from the group consisting of

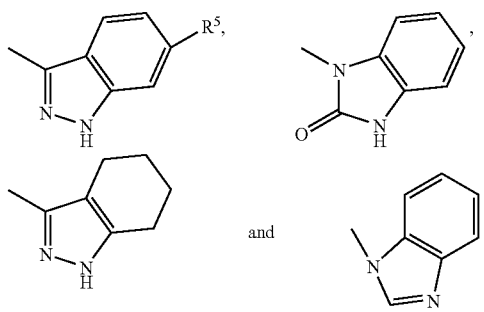

wherein R⁵ is selected from H and F; and

Z is selected from hydrogen and $C_1$-$C_6$ alkoxy.

In a fifth embodiment, there is provided a method for treating a obesity, diabetes, pain, inflammation, depression, and anxiety, which method comprises the administration to a mammal, including a human, of a therapeutically effective amount of a compound of Formula 1a, a salt, solvate, or physiological derivative thereof.

In a sixth aspect of the present invention, there is provided the use of a compound of formula (Ia), or a salt, solvate, or a physiologically functional derivative thereof in the preparation of a medicament for use in the treatment of a disorder mediated by MC4R and/or MC1R.

In a seventh embodiment, there is provided the use of a compound of formula (Ia), or a salt, solvate, or a physiologically functional derivative thereof in the preparation of a medicament for use in the treatment of obesity, diabetes, inflammation, pain, depression, and anxiety.

In still a further embodiment of the invention there is provided processes for the preparation of a compound of Formula 1a physiologically acceptable salt, solvate, or physiologically functional derivative thereof.

DETAILED DESCRIPTION OF THE INVENTION

As used herein, "a compound of the invention" or "a compound of Formula 1 or 1a" means a compound of Formula 1 or 1a or a pharmaceutically acceptable salt, solvate, or physiologically functional derivative (such as, e.g., a prodrug), thereof.

As used herein, the term "optionally" means that the subsequently described event(s) may or may not occur, and includes both event(s) that occur and events that do not occur.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing prevention, or amelioration of a disease, disorder, or side effect, or a decrease in the rate of advancement of a disease or disorder. The term also includes within its scope amounts effective to enhance normal physiological function.

As used herein, unless otherwise specified, the term "alkyl" and "alkylene" refer to straight or branched chain hydrocarbyl radical containing the specified number of carbon atoms. Examples of "alkyl" as used herein include, but are not limited to, methyl, ethyl, n-propyl, n-butyl, n-pentyl, isobutyl, isopropyl, tert-butyl, and hexyl.

As used herein, unless otherwise specified, the term "alkenyl" refers to straight or branched hydrocarbon chains containing the specified number of carbon atoms and at least one and up to three carbon-carbon double bonds. Examples of "alkenyl" as used herein include, but are not limited to, ethenyl and propenyl.

Unless otherwise specified, the term "aryl", as used herein, refers to monocyclic carbocyclic groups and fused bicyclic carbocyclic groups having the specified number of ring atoms and having at least one aromatic ring. Examples of particular aryl groups include, but are not limited to, phenyl and napthyl.

The term "heteroaryl", unless otherwise specified, refers to aromatic monocyclic groups and aromatic fused bicyclic groups having at least one aromatic ring having the specified number of ring members (e.g., carbon and heteroatoms N, O, and/or S) and containing 1, 2, 3, or 4 heteroatoms selected from N, O, and S. Examples of particular heteroaryl groups include, but are not limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, benzazepine, benzimidazole, benzoximidazole, indole, oxindole and indazole.

As used herein, the terms "$C_{1-6}$haloalkyl" refers to an alkyl group as defined above containing at least 1, and at most 6 carbon atoms respectively substituted with at least one halo group, halo being as defined herein. Examples of such branched or straight chained haloalkyl groups useful in the present invention include, but are not limited to methyl, ethyl, propyl, isopropyl, isobutyl and n-butyl substituted independently with one or more halos, e.g. fluoro, chloro, bromo and iodo.

As used herein, the term "alkoxy" refers to the group RaO—, where Ra is alkyl as defined above and the terms "$C_1$-$C_3$alkoxy" and "$C_1$-$C_6$alkoxy" refer to an alkoxy group as defined herein wherein the alkyl moiety contains at least 1, and at most 3 or 6, carbon atoms. Exemplary "$C_1$-$C_3$alkoxy" and "$C_1$-$C_6$alkoxy" groups useful in the present invention include, but are not limited to methoxy, ethoxy, n-propoxy, isopropoxy, n-butoxy, and t-butoxy.

As used herein, the term "amino" refers to the group —$NH_2$.

As used herein the term "alkylamino" refers to the group —NHRa wherein Ra is alkyl as defined.

As used herein, the term "haloalkoxy" refers to the group $R^aO$—, where Ra is haloalkyl as defined above and the term "$C_1$-$C_6$haloalkoxy" refers to a haloalkoxy groups as defined herein wherein the haloalkyl moiety contains at least 1, and at most 6, carbon atoms. Exemplary $C_1$-$C_6$haloalkoxy groups useful in the present invention include, but is not limited to, trifluoromethoxy.

As used herein, the term "alkylsulfanyl" refers to the group RaS—, where Ra is alkyl as defined above and the terms "$C_1$-$C_6$alkylsulfanyl" refers to an alkylsulfanyl group as defined herein wherein the alkyl moiety contains at least 1, and at most 6, carbon atoms.

As used herein, the term "cyano" refers to the group —CN.

As used herein, the terms "halo" or "halogen" refer to fluorine, chlorine, bromine, and iodine. Preferred among these are chlorine (or "chloro") and fluorine (or "fluoro").

Preferably Ar represents phenyl or 2, 3 or 4 pyridyl group, each of which may be optionally substituted by one to four substituents each independently selected from halo, $C_1$-$C_3$alkoxy or $C_1$-$C_3$alkyl. More preferably Ar represents a phenyl group optionally substituted by one to four substituents independently selected from halo and methoxy. Most preferably Ar is phenyl.

Preferably $R^1$ is H or $C_1$-$C_6$alkyl most preferably methyl. When $R^2$, N and $R^3$ form a 6 or 7 membered ring, preferably $R^1$ is H or methyl, most preferably H.

Preferably n is 0 or 1;

Preferably each $R^4$ is independently selected from $C_1$-$C_4$alkyl, $C_1$-$C_4$alkoxy, hydroxy, halo $C_1$-$C_3$haloalkoxy. Preferably when n is 1, $R^4$ is on the 4 position on the ring.

Preferably $R^2$ is H or $C_1$-$C_6$alkyl, more preferably methyl.

In an alternative aspect, preferably, Q is selected from the group consisting of N-isopropylaniline, N-isopropyl-p-methoxyaniline, and tetrahydrobenzazepine. Most preferably, Q is tetrahydrobenzazepine for MC1R activity; and Q is N-isopropylaniline, or N-isopropyl-p-methoxyaniline for MC4R activity.

Preferably Y is

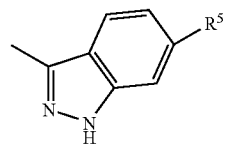

Preferably Z is H or methoxy, in a preferred aspect Z is H to give MC1R activity and Z is methoxy for MC4R activity.

While the preferred groups for each variable have generally been listed above separately for each variable, preferred compounds of this invention include those in which several or each variable in Formula (1 and 1a) is selected from the preferred, more preferred, or most preferred groups for each variable. Therefore, this invention is intended to include all combinations of preferred, more preferred, and most preferred groups.

Specific compounds of Formula 1 and 1a include, but are not limited to, those set forth in Table 1 below and/or those compounds set forth in the examples.

Table 1: Illustrative Compounds of the Invention

In Table 1, compounds finding utility as MC4R agonists are exemplified as numbered compounds 1 through 8. In Table 1, compounds finding utility as MC1R agonists are exemplified as numbered compounds 9 through 32.

| Example # | Structure | Name |
|---|---|---|
| 1 | 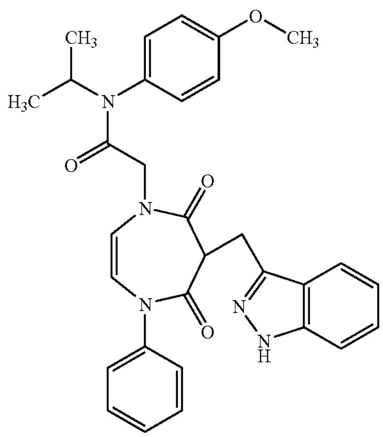 | 2-[2,4-dioxo-3-(1H-indazol-3-ylmethylene)-5-phenyl-2,3,4,5-tetrahydro-1H-1,5-diazepin-1-yl]-N-isopropyl-N-(4-methoxyphenyl)acetamide |
| 2 | 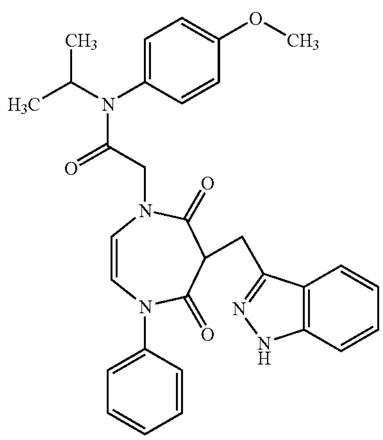 | (Chiral) 2-[2,4-dioxo-3-(1H-indazol-3-ylmethylene)-5-phenyl-2,3,4,5-tetrahydro-1H-1,5-diazepin-1-yl]-N-isopropyl-N-(4-methoxyphenyl)acetamide |
| 3 | 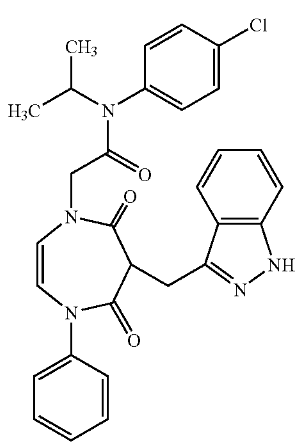 | 2-[2,4-dioxo-3-(1H-indazol-3-ylmethylene)-5-phenyl-2,3,4,5-tetrahydro-1H-1,5-diazepin-1-yl]-N-(4-chlorophenyl)-N-isopropylacetamide |

| Example # | Structure | Name |
|---|---|---|
| 4 | 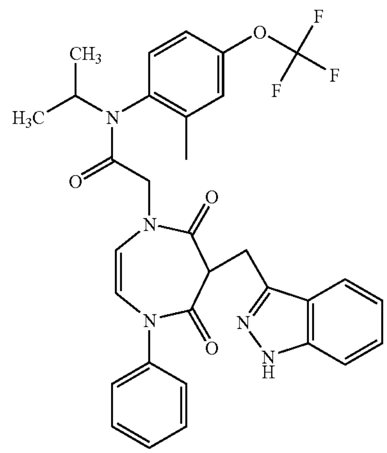 | 2-[2,4-dioxo-3-(1H-indazol-3-ylmethylene)-5-phenyl-2,3,4,5-tetrahydro-1H-1,5-diazepin-1-yl]-N-isopropyl-N-(2-methyl-4-trifluoromethoxy)phenyl) acetamide |
| 5 | 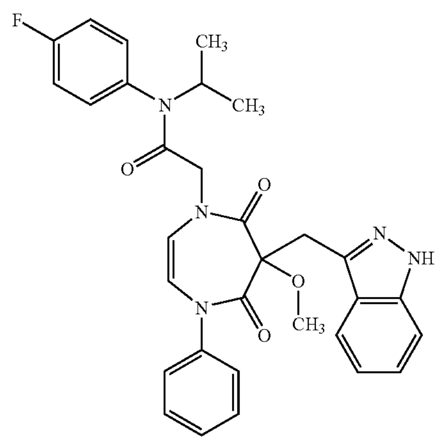 | 2-[2,4-dioxo-3-(1H-indazol-3-ylmethylene)-3-methoxy-5-phenyl-2,3,4,5-tetrahydro-1H-1,5-diazepin-1-yl]-N-(4-fluorophenyl) N-isopropylacetamide |
| 6 | 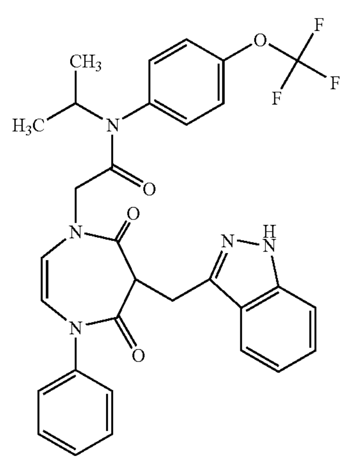 | 2-[2,4-dioxo-3-(1H-indazol-3-ylmethylene)-5-phenyl-2,3,4,5-tetrahydro-1H-1,5-diazepin-1-yl]-N-isopropyl-N-(4-(trifluoromethoxyphenyl) acetamide |

-continued
| Example # | Structure | Name |
|---|---|---|
| 7 | 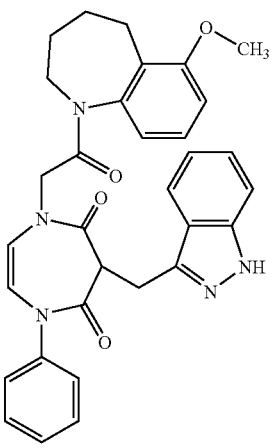 | 3-(1H-indazol-3-ylmethylene)-1-[2-(6-methoxy-2,3,4,5-tetrahydro-1H-1-benzazepin-1-yl)-2-oxoethyl]-5-phenyl-1H-1,5-diazepine-2,4-dione |
| 8 | 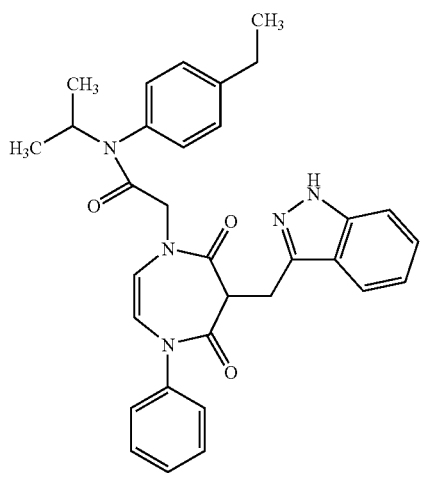 | 2-[2,4-dioxo-3-(1H-indazol-3-ylmethylene)-5-phenyl-2,3,4,5-tetrahydro-1H-1,5-diazepin-1-yl]-N-(4-ethylphenyl)-N-isopropylacetamide |
| 9 | 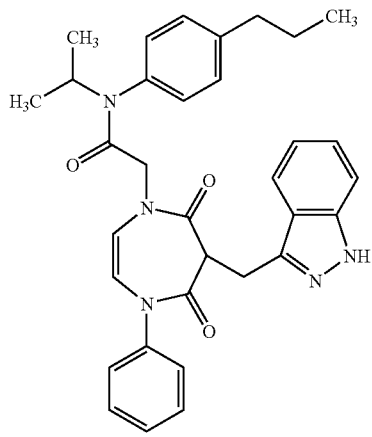 | 2-[2,4-dioxo-3-(1H-indazol-3-ylmethylene)-5-phenyl-2,3,4,5-tetrahydro-1H-1,5-diazepin-1-yl]-N-isopropyl-N-(4-propylphenyl)acetamide |

-continued

| Example # | Structure | Name |
|---|---|---|
| 10 | 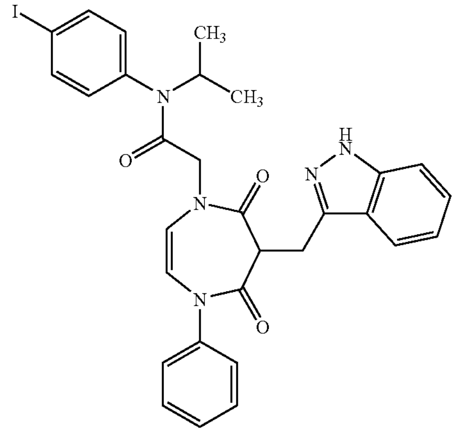 | 2-[2,4-dioxo-3-(1H-indazol-3-ylmethylene)-5-phenyl-2,3,4,5-tetrahydro-1H-1,5-diazepin-1-yl]-N-(4-iodophenyl)-N-isopropylacetamide |
| 11 | 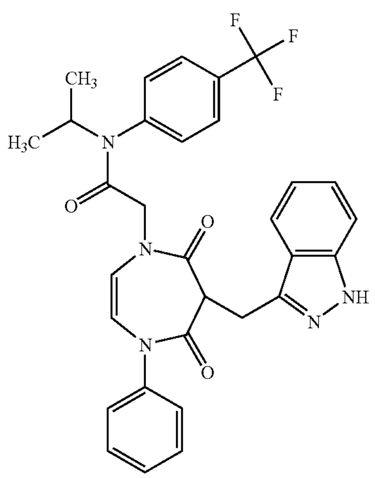 | 2-[2,4-dioxo-3-(1H-indazol-3-ylmethylene)-5-phenyl-2,3,4,5-tetrahydro-1H-1,5-diazepin-1-yl]-N-isopropyl-N-(4-trifluoromethylphenyl)acetamide |
| 12 | 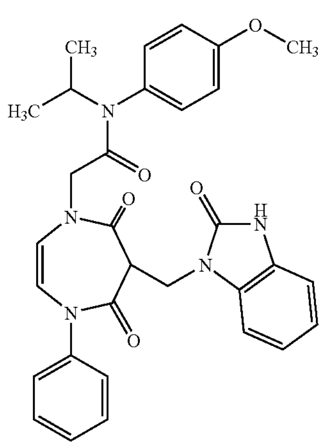 | 2-[2,4-dioxo-3-(2,3-dihydro-2-oxo-1H-benzimidazol-1-yl)methylene-5-phenyl-2,3,4,5-tetrahydro-1H-1,5-diazepin-1-yl]-N-isopropyl-N-(4-methoxyphenyl)acetamide |

| Example # | Structure | Name |
|---|---|---|
| 13 | 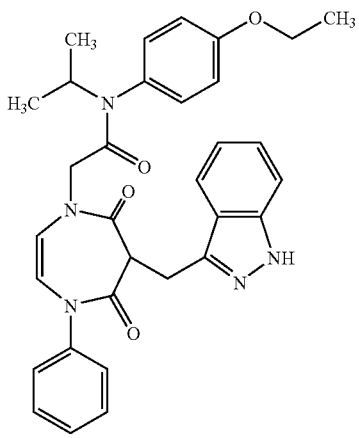 | 2-[2,4-dioxo-3-(1H-indazol-3-ylmethylene)-5-phenyl-2,3,4,5-tetrahydro-1H-1,5-diazepin-1-yl]-N-(4-ethoxyphenyl)-N-isopropylacetamide |
| 14 | 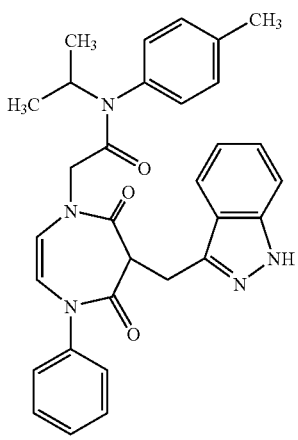 | 2-[2,4-dioxo-3-(1H-indazol-3-ylmethylene)-5-phenyl-2,3,4,5-tetrahydro-1H-1,5-diazepin-1-yl]-N-isopropyl-N-(4-methylphenyl)acetamide |
| 15 | 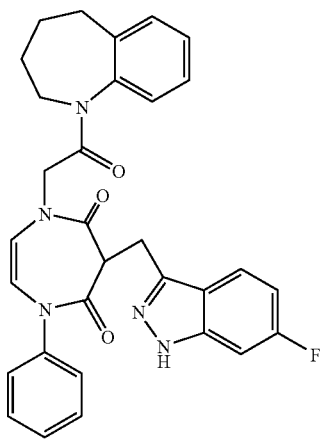 | 3-(6-fluoro-1H-indazol-3-ylmethylene)-1-[2-oxoethyl-2-(2,3,4,5-tetrahydro-1H-1-benzazepin-1-yl)]-5-phenyl-1H-1,5-diazepine-2,4-dione |

| Example # | Structure | Name |
|---|---|---|
| 16 | 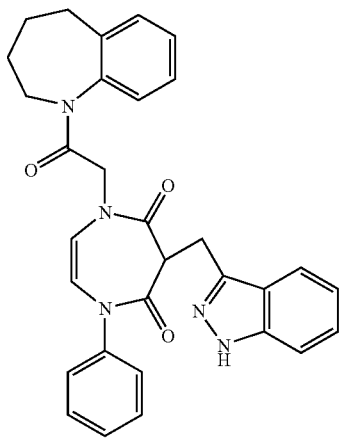 | 3-(1H-indazol-3-ylmethylene)-1-[2-oxoethyl-2-(2,3,4,5-tetrahydro-1H-1-benzazepin-1-yl)]-5-phenyl-1H-1,5-diazepine-2,4-dione |
| 17 | 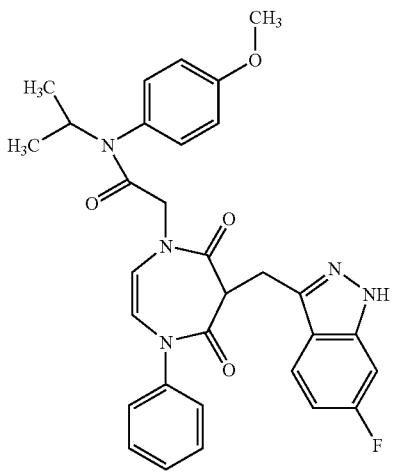 | 2-[2,4-dioxo-3-(6-fluoro-1H-indazol-3-ylmethylene)-5-phenyl-2,3,4,5-tetrahydro-1H-1,5-diazepin-1-yl]-N-isopropyl-N-(4-methoxyphenyl)acetamide |
| 18 | 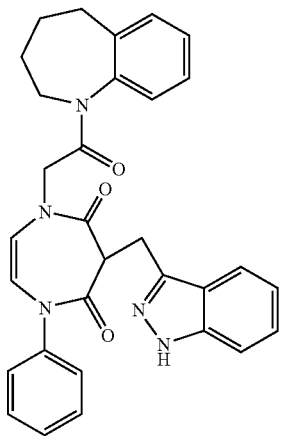 | (Chiral) 3-(1H-indazol-3-ylmethylene)-1-[2-oxoethyl-2-(2,3,4,5-tetrahydro-1H-1-benzazepin-1-yl)]-5-phenyl-1H-1,5-diazepine-2,4-dione |

-continued

| Example # | Structure | Name |
|---|---|---|
| 19 | 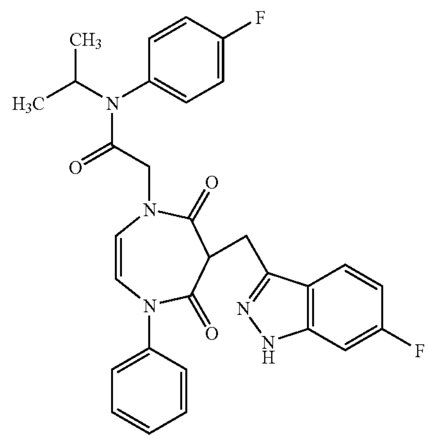 | 2-[2,4-dioxo-3-(6-fluoro-1H-indazol-3-ylmethylene)-5-phenyl-2,3,4,5-tetrahydro-1H-1,5-diazepin-1-yl]-N-(4-fluorophenyl)-N-isopropylacetamide |
| 20 | 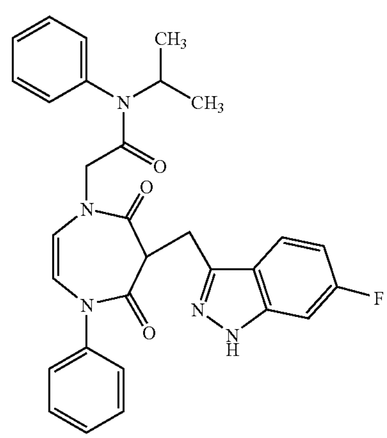 | 2-[2,4-dioxo-3-(6-fluoro-1H-indazol-3-ylmethylene)-5-phenyl-2,3,4,5-tetrahydro-1H-1,5-diazepin-1-yl]-N-isopropyl-N-phenylacetamide |
| 21 | 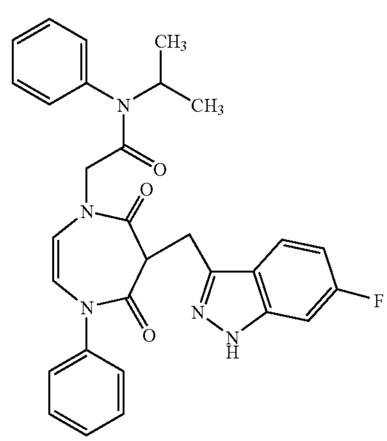 | (Chiral) 2-[2,4-dioxo-3-(6-fluoro-1H-indazol-3-ylmethylene)-5-phenyl-2,3,4,5-tetrahydro-1H-1,5-diazepin-1-yl]-N-isopropyl-N-phenylacetamide |

-continued
| Example # | Structure | Name |
|---|---|---|
| 22 | 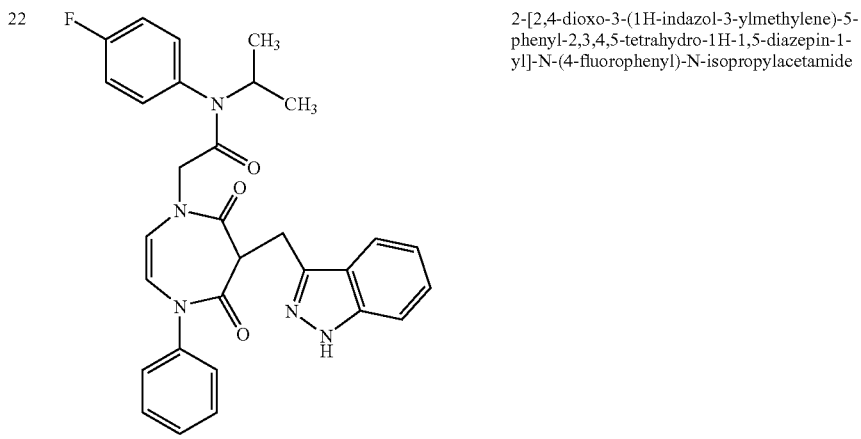 | 2-[2,4-dioxo-3-(1H-indazol-3-ylmethylene)-5-phenyl-2,3,4,5-tetrahydro-1H-1,5-diazepin-1-yl]-N-(4-fluorophenyl)-N-isopropylacetamide |
| 23 | 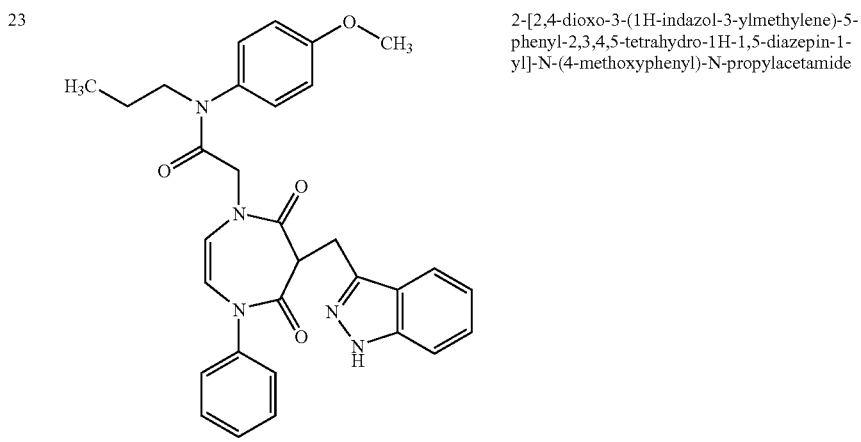 | 2-[2,4-dioxo-3-(1H-indazol-3-ylmethylene)-5-phenyl-2,3,4,5-tetrahydro-1H-1,5-diazepin-1-yl]-N-(4-methoxyphenyl)-N-propylacetamide |
| 24 | 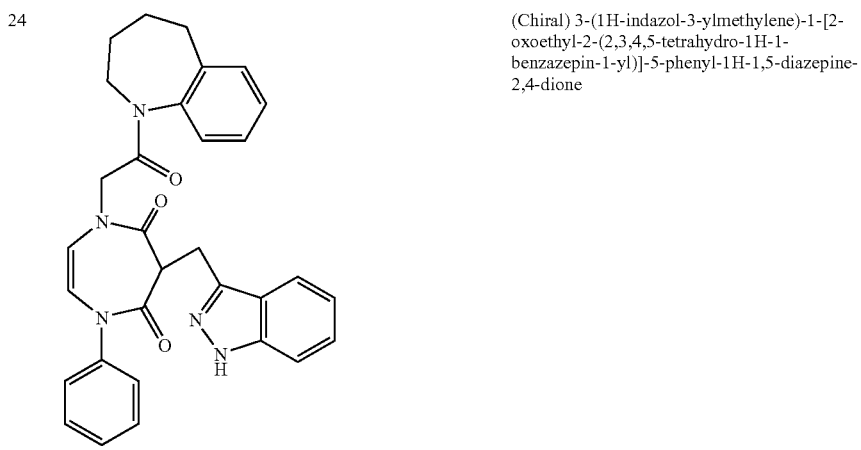 | (Chiral) 3-(1H-indazol-3-ylmethylene)-1-[2-oxoethyl-2-(2,3,4,5-tetrahydro-1H-1-benzazepin-1-yl)]-5-phenyl-1H-1,5-diazepine-2,4-dione |

| Example # | Structure | Name |
|---|---|---|
| 25 | 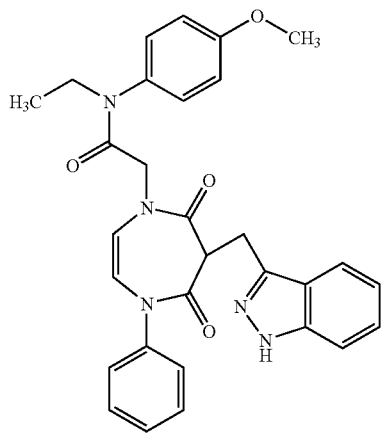 | 2-[2,4-dioxo-3-(1H-indazol-3-ylmethylene)-5-phenyl-2,3,4,5-tetrahydro-1H-1,5-diazepin-1-yl]-N-ethyl-N-(4-methoxyphenyl)acetamide |
| 26 | 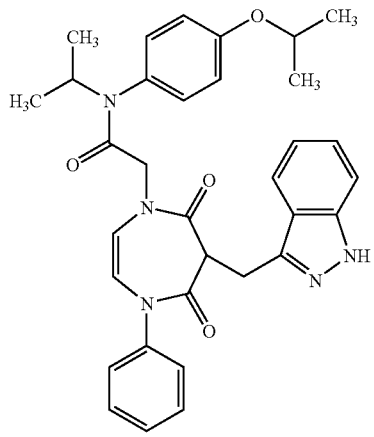 | 2-[2,4-dioxo-3-(1H-indazol-3-ylmethylene)-5-phenyl-2,3,4,5-tetrahydro-1H-1,5-diazepin-1-yl]-N-(4-isopropoxyphenyl)-N-isopropylacetamide |
| 27 | 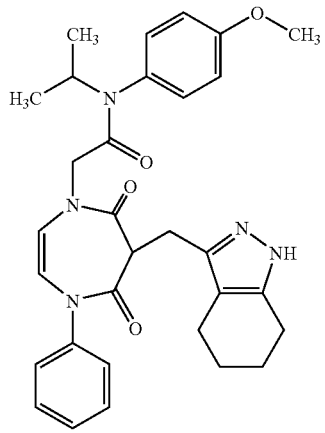 | 2-[2,4-dioxo-5-phenyl-3-(4,5,6,7-tetrahydro-1H-indazol-3-ylmethylene)-2,3,4,5-tetrahydro-1H-1,5-diazepin-1-yl]-N-isopropyl-N-(4-methoxyphenyl)acetamide |

| Example # | Structure | Name |
|---|---|---|
| 28 | 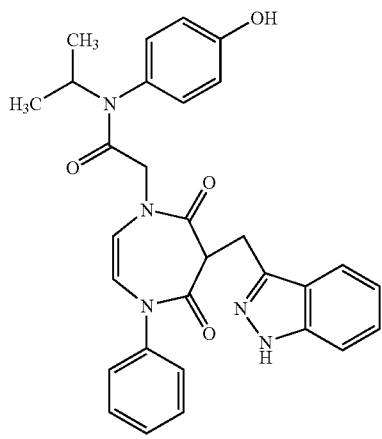 | (Chiral) 2-[2,4-dioxo-3-(1H-indazol-3-ylmethylene)-5-phenyl-2,3,4,5-tetrahydro-1H-1,5-diazepin-1-yl]-N-(4-hydroxyphenyl)-N-isopropylacetamide |
| 29 | 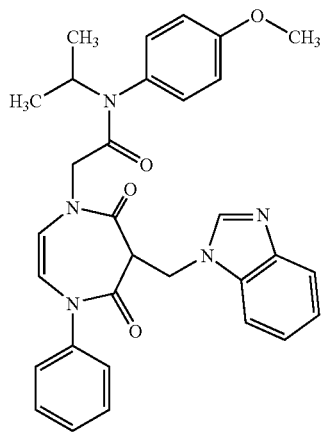 | 2-[2,4-dioxo-3-(1H-benzimidazol-1-ylmethylene)-5-phenyl-2,3,4,5-tetrahydro-1H-1,5-diazepin-1-yl]-N-isopropyl-N-(4-methoxyphenyl)acetamide |
| 30 | 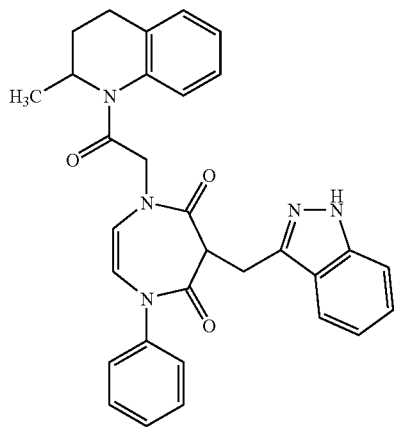 | 1-[2-(3,4-dihydro-2H-2-methylquinolin-1-yl)-2-oxoethyl]-3-(1H-indazol-3-ylmethylene)-5-phenyl-1H-1,5-diazepine-2,4-dione |

-continued

| Example # | Structure | Name |
|---|---|---|
| 31 | 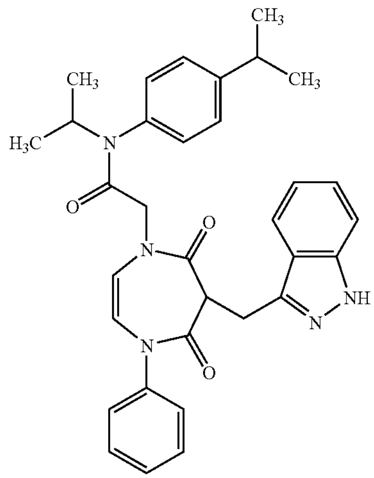 | 2-[2,4-dioxo-3-(1H-indazol-3-ylmethylene)-5-phenyl-2,3,4,5-tetrahydro-1H-1,5-diazepin-1-yl]-N-isopropyl-N-(4-isopropylphenyl)acetamide |
| 32 | 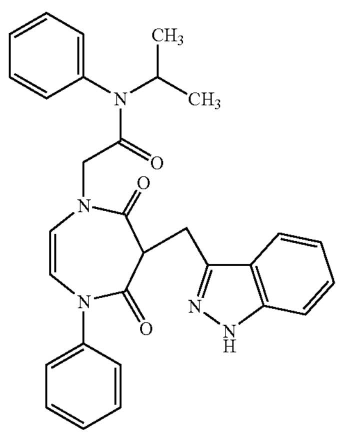 | (Chiral) 2-[2,4-dioxo-3-(1H-indazol-3-ylmethylene)-5-phenyl-2,3,4,5-tetrahydro-1H-1,5-diazepin-1-yl]-N-isopropyl-N-phenylacetamide |

Certain compounds of Formula 1 may exist in stereoisomeric forms. The individual stereoisomers (enantiomers and diasteromers) and mixtures of these are included within the scope of the present invention. The present invention also covers the individual isomers of the compounds represented by Formula 1 as well as mixtures with isomers thereof in which one or more chiral centers are inverted. Certain compounds of Formula 1 may be prepared as regioisomers. The present invention covers both the mixture of regioisomers as well as individual compounds. When a compound of formula (I) is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See, for example, *Stereochemistry of Carbon Compounds* by E. L. Eliel (Mcgraw Hill, 1962) and *Tables of Resolving Agents* by S. H. Wilen. Likewise, it is understood that compounds of Formula 1 may exist in tautomeric forms other than that shown in the formula and these are also included within the scope of the present invention. It is to be understood that the present invention includes all combinations and subsets of the particular groups defined herein above.

It will be appreciated by those skilled in the art that the compounds of the present invention may also be utilized in the form of a pharmaceutically acceptable salt, solvate or physiologically functional derivative thereof (e.g., a prodrug).

As used herein, the term "solvate" refers to a complex of variable stoichiometry formed by a solute (in this invention, a compound of formula (I) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

It will also be appreciated by those skilled in organic chemistry that many organic compounds can exist in more than one crystalline form. For example, crystalline form may vary from solvate to solvate. Thus, all crystalline forms of the compounds of formula (I) or the pharmaceutically acceptable solvates thereof are within the scope of the present invention.

It will be appreciated by a person skilled in the art that the compounds of the invention may be utilised in the form of a pharmaceutically acceptable salt, solvate or physiologically functional derivative thereof.

The term "physiologically functional derivative" as used herein refers to any pharmaceutically acceptable derivative of a compound of the present invention, for example, a ester or an amide of a compound of Formula 1, which upon administration to an animal, particularly a mammal, such as a human, is capable of providing (directly or indirectly) a compound of the present invention or an active metabolite thereof. See, for example, *Burger's Medicinal Chemistry and Drug Discovery*, 5th Edition, Vol. 1: Principles and Practice.

Processes for preparing pharmaceutically salts, solvates, and physiologically functional derivatives of the compounds of Formula 1 are conventional in the art. See, for example, *Burger's Medicinal Chemistry and Drug Discovery*, 5th Edition, Vol. 1: Principles and Practice.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally; with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 200 mg/kg body weight of recipient (mammal) per day and more usually in the range of 1 to 100 mg/kg body weight per day. Thus, for a 70 kg adult mammal, the actual amount per day would usually be from 70 mg to 7 g and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

Compounds of Formula 1a are believed to have a role in the treatment of MC4R and/or MC1R mediated diseases. As used herein, the term "treatment" refers to alleviating a specified condition or disease, eliminating or reducing the symptoms of such condition or disease, slowing or eliminating the progression of the disease or condition, and/or preventing or delaying the reoccurrence of the condition or disease in a patient or subject.

Compounds of the present invention are agonists of melanocortin-4 and/or melanocortin-1 receptors and can be used for the treatment of a disease caused by or attributable to a POMC and/or MC4R and MC1R activities. Accordingly, compounds of the invention may reduce hunger, suppress appetite, control eating, and/or induce satiety. Therefore, the present invention provides methods for the treatment of several conditions or diseases such as obesity, diabetes, inflammation, pain, depression (e.g., major depression and/or bipolar disorder), and/or anxiety.

Such treatment comprises the administration of a therapeutically effective amount of a compound of Formula 1a, preferably in the form of a salt, solvate, or physiologically functional derivative thereof to a mammal, especially a human. As used herein, the term "therapeutically effective amount" means an amount of a compound of Formula 1 which is sufficient, in the patient (mammal) to which it is administered, to elicit a biological or medical response in a cell, cell culture, animal or cell tissue, biological system, animal (including human) that is being sought, for instance by a researcher, clinician, or physician.

The present invention thus also provides compounds of formula (Ia) and pharmaceutically acceptable salts or solvates thereof, or physiologically functional derivatives thereof, for use in medical therapy, and particularly in the treatment of disorders mediated by MCR4 and/or MC1R.

The present invention is directed to methods of regulating, modulating, or inhibiting MC4R and/or MC1R for the prevention and/or treatment of disorders related to MC4R and/or MC1R. In particular, the compounds of the present invention can also be used in the treatment of obesity, diabetes, inflammation, pain, depression (e.g., major depression and/or bipolar disorder), and/or anxiety.

A further aspect of the invention provides a method of treatment of a mammal suffering from a disorder mediated by MC4R and/or MC1R, which includes administering to said subject an effective amount of a compound of formula (Ia) or a pharmaceutically acceptable salt, solvate, or a physiologically functional derivative thereof. In a preferred embodiment, the disorder is a susceptible cancer.

A further aspect of the present invention provides the use of a compound of formula (Ia), or a pharmaceutically acceptable salt or solvate thereof, or a physiologically functional derivative thereof, in the preparation of a medicament for the treatment of a disorder mediated by MC4R and/or MC1R.

The compounds for formula (Ia) for use in the instant invention may be used in combination with one or more other therapeutic agents for example, compounds employed in the treatment of diabetes, obesity, arteriosclerosis and/or hypertension. The compounds of the invention may also be used in combination with therapeutic agents useful in pain and/or inflammation. Further combinations include combinations with a diuretic fiber of anti-emetics. The invention thus provides in a further aspect the use of a combination comprising a compound of formula (Ia) with a further therapeutic agent in the treatment of MC4R and/or MC1R mediated diseases.

When the compounds of formula (Ia) are used in combination with other therapeutic agents, the compounds may be administered either sequentially or simultaneously by any convenient route.

The combinations referred to above may conveniently be presented for use in the form of a pharmaceutical formulation and this pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (Ia) is used in combination with a second therapeutic agent active against the same disease, the dose of each compound may differ from that when the compound is used alone. Appropriate doses will be readily appreciated by those skilled in the art.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of general formula (I) and (1a) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I) and (Ia). Those skilled in the art will recognize if a stereocenter exists in compounds of Formula (I) and (Ia). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Compounds of Formula I and (Ia) can be prepared according to the synthetic sequences illustrated in Schemes detailed below and further detailed in the Examples section following.

First Preparation. Compounds of Formula I and (Ia) especially wherein Y is

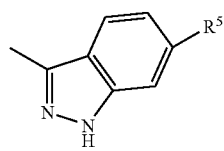

can be prepared in accordance with the Reaction Schematic 1 set forth below and wherein Ar, Y, Z, $R^1$, $R^2$, and $R^3$ are as defined in Formula I and Ia. This is illustrated by a specific example of Q but any Q as defined above may be substituted. Thus, compounds may be prepared by reaction of an aldehyde-protected arylamine of formula (a) with a methyl malonylchloride of formula (b) in the presence of base, to give the methyl malonyl amide of formula (c). Subsequent ester hydrolysis afforded the malonic mono-amide, mono-carboxylic acid of formula (d).

Separately, the 2-bromoacetamide(s) of formula (e) were prepared by the methods described in patent application WO 96/11940. Aminolysis of the compound of formula (e) afforded the N-substituted glycine derivatives of formula (f).

Coupling of the malonic mono-amide, mono-carboxylic acid of formula (d) with the N-substituted glycine derivatives of formula (f), in the presence of one or more (preferably two) amide-forming coupling reagents, yielded a compound of formula (g). Subsequent alkylation of the compound of formula (g) with amine-protected bromomethylene aryl of formula (h), prepared as described in patent application WO 95/28391, provided a racemic mixture of compounds of formula (i). Treatment of compounds of formula (i) with acids led to the deprotection of the aldehyde and amine protecting groups, followed by acid-catalyzed aldehyde and amide cyclization to give the 2,4-dioxo-1,5-diazepine compounds, also named 1,5-diazepine-2,4-diones, of Formula (Ia).

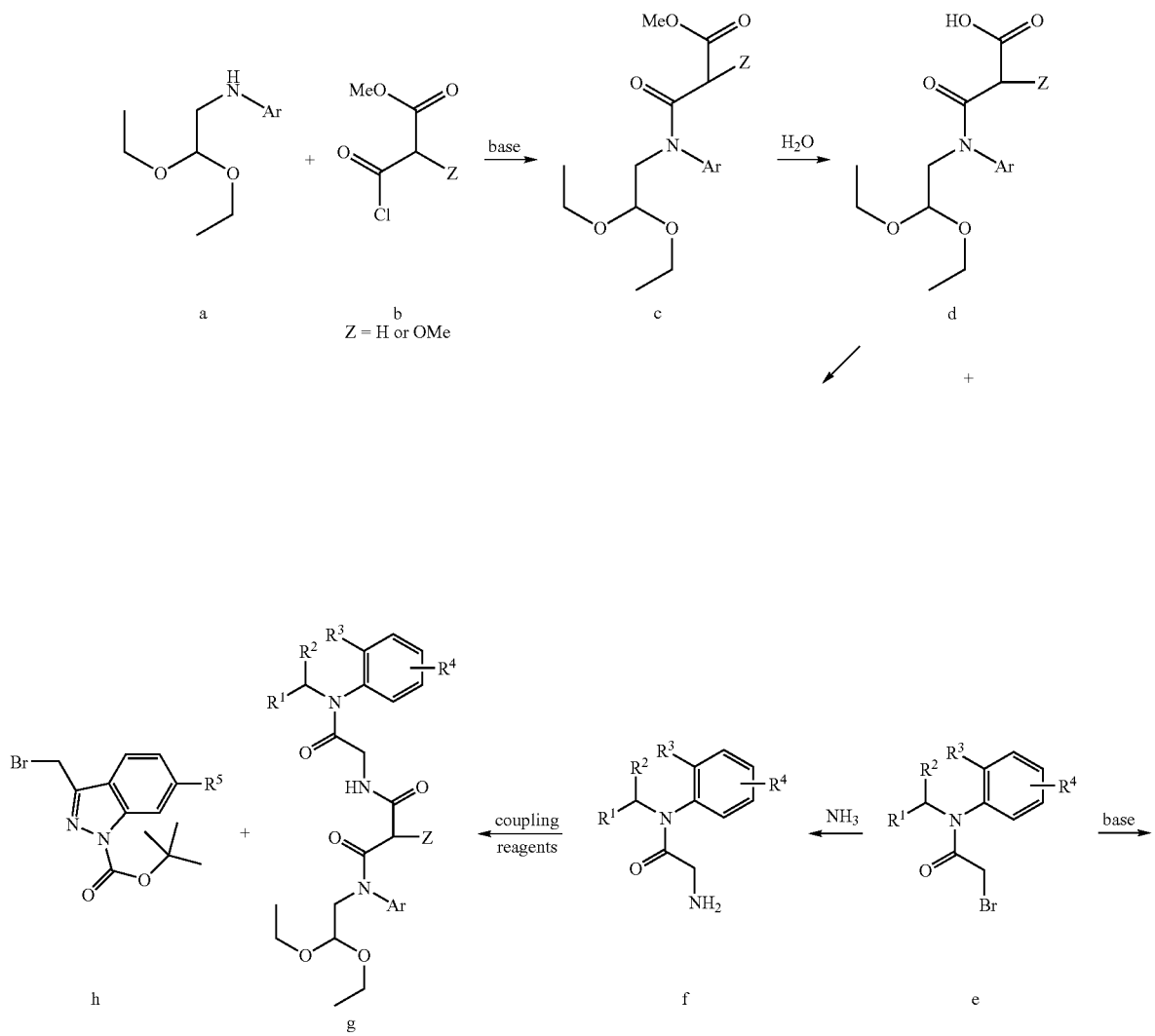

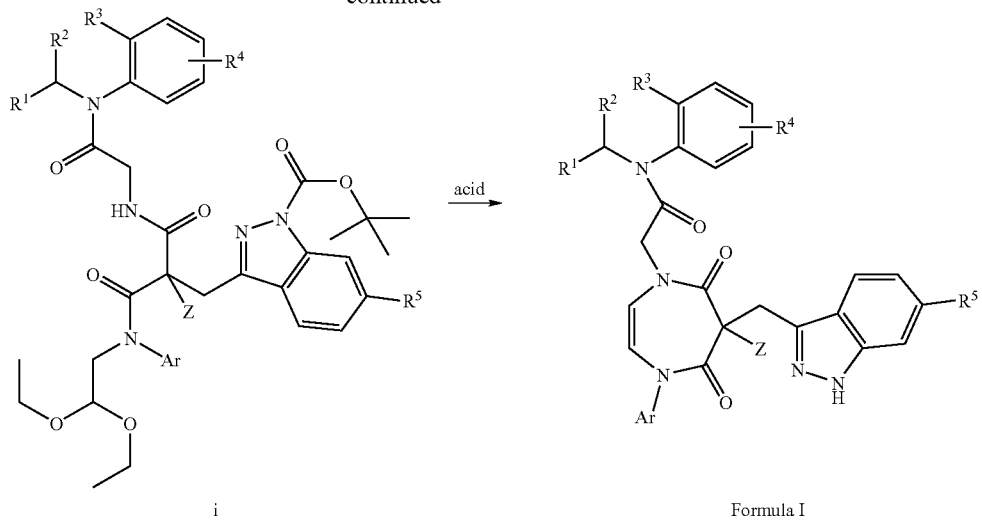

i → Formula I

Second Preparation. Compounds of Formula 1 and 1a especially where Y is

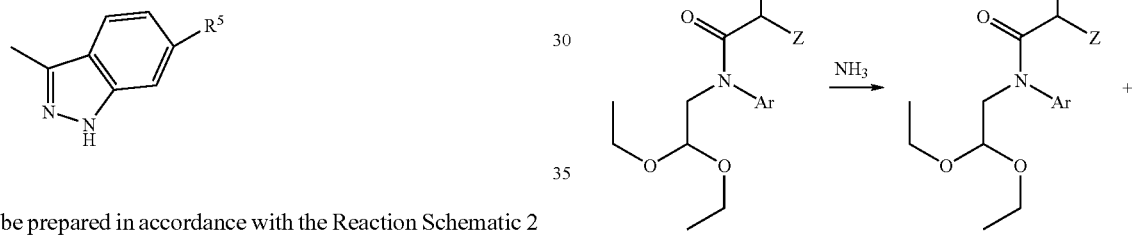

can be prepared in accordance with the Reaction Schematic 2 set forth below. This is illustrated with a specific example of Q but any Q may be substituted. Thus, compounds of Formula (Ia) may be prepared by reaction of an aldehyde-protected arylamine of formula (a) with methyl malonyl chloride of formula (b) to give the methyl malonyl amide (c). Aminolysis of the compound of formula (c) afforded the unsymmetrical malonic diamide of formula (j). Subsequent alkylation of the compound of formula (j) with the amine-protected bromomethylene aryl of formula (h) and a base provided a compound of formula (k). Treatment of the compound of formula (k) with an acid leads to the deprotection of the aldehyde protecting group, followed by acid-catalyzed aldehyde and amide cyclization, to give the 2,4-dioxo-1,5-diazepine compound (I). Subsequent alkylation with bromoacetamides of formula (e) produced the compounds.

Reaction Schematic 2

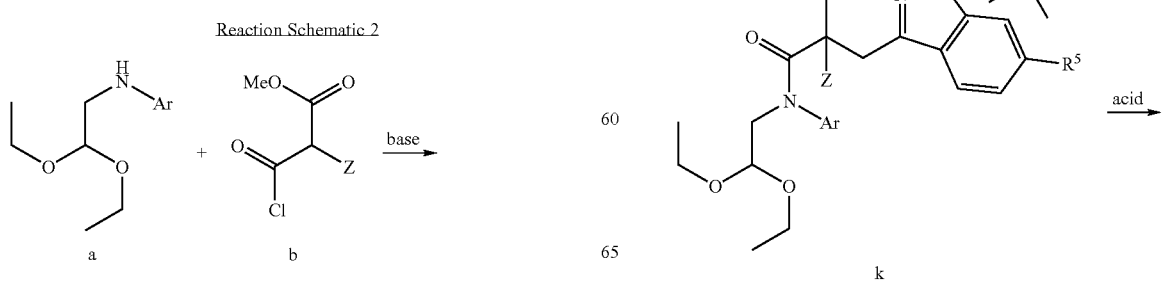

-continued

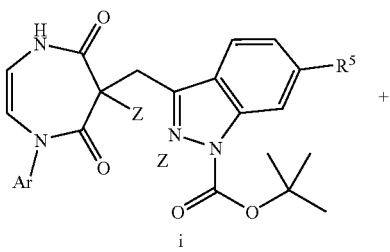
i

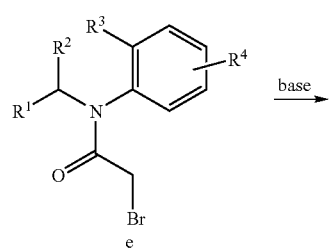
e

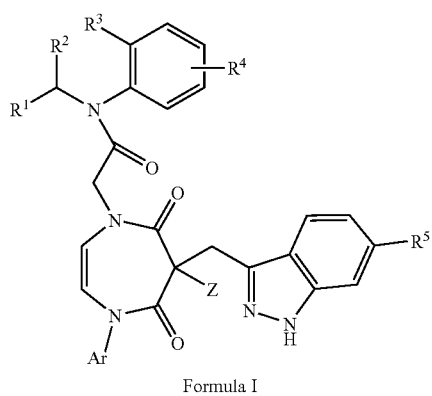
Formula I

Third Preparation. Compounds of Formula I (specifically compounds where Y is)

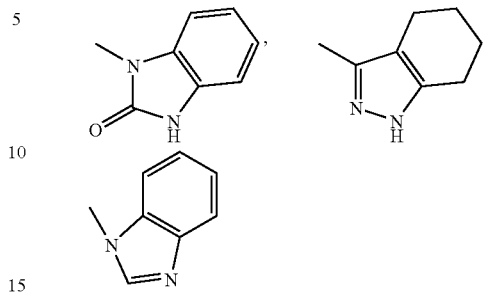

can be prepared in accordance with the Reaction Schematic 3 set forth below. Thus, the compound of formula (j) is reacted with trimethylene dithiotosylate yielding the cyclic disulfide compound of formula (m). Treatment of the compound of formula (m) with an acid leads to the deprotection of the aldehyde protecting group, followed by acid-catalyzed aldehyde and amide cyclization, to give the 2,4-dioxo-1,5-diazepine compound of formula (n). The diazepine of formula (n) is then N-alklyated with base and the 2-bromoacetamides of formula (e) to yield the N-glycine linked compounds of formula (o). Compound(s) of formula (o) were then reduced to remove the cyclic disulfide moiety and produce the 2,4-dioxo-1,5-diazepine compounds of formula (p). Alkylation of compounds (p) with LG-CH$_2$—Y and base then afforded the compounds of Formula 1C, wherein Ar and Y can be the same or different moiety as set forth for Ar in Formula 1.

Alternatively, the compounds of formula (p) can be alkylated with a protected methyleneoxy alkylation agent (e.g., LGCH$^2$OPG, where LG is a leaving group and PG is a protecting group) to give compound(s) of formula (q). Deprotection of the protected methyleneoxy moiety in the presence of acid afforded the hydroxymethylene-containing compound(s) of formula (r). The compound(s) of formula (r) were then esterified with methanesulfonic acid (or reacted with methanesulfonyl chloride) to yield the compound(s) of formula (s). Displacement of the methanesulfonate moiety with either benzimidazole or benzoximidazole then afforded the compounds of Formula 1D.

Reaction Schematic 3

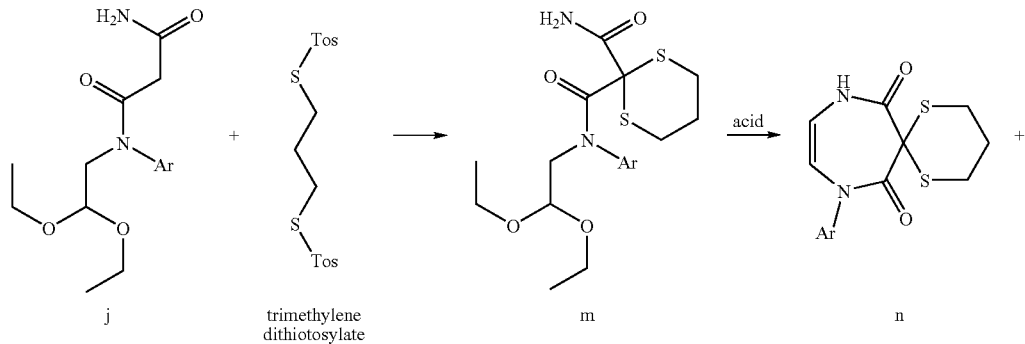

j    trimethylene dithiotosylate    m    n

-continued
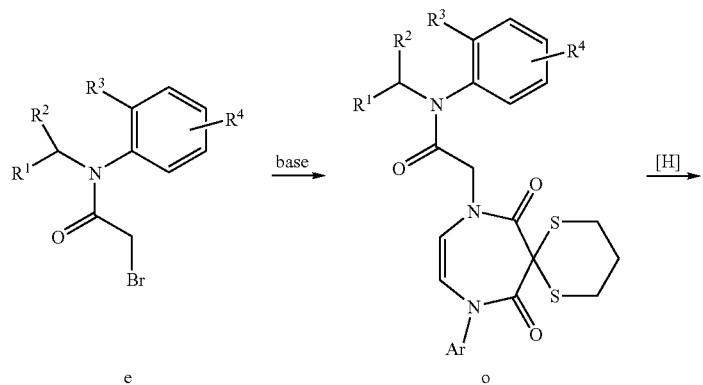
e → o
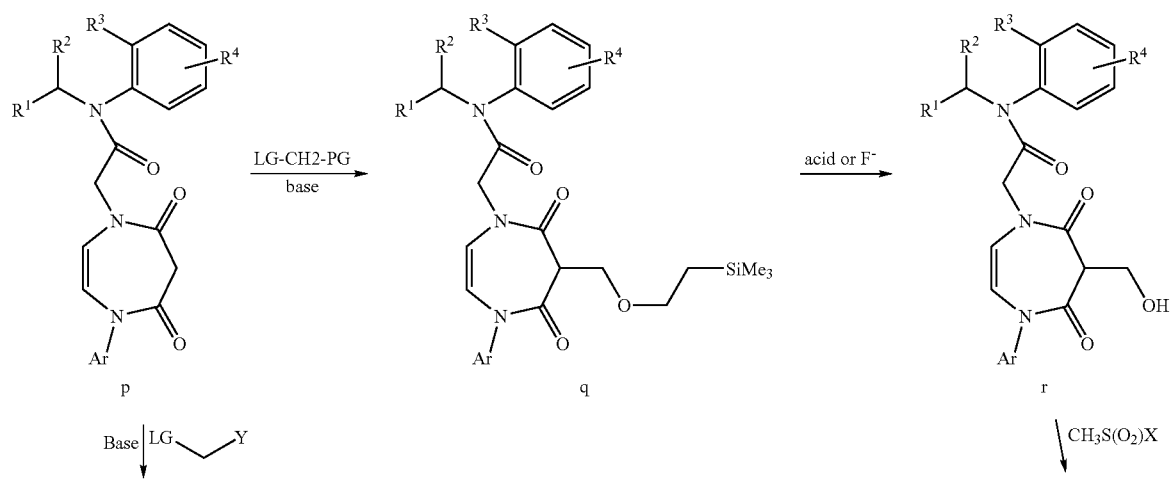
p → q → r
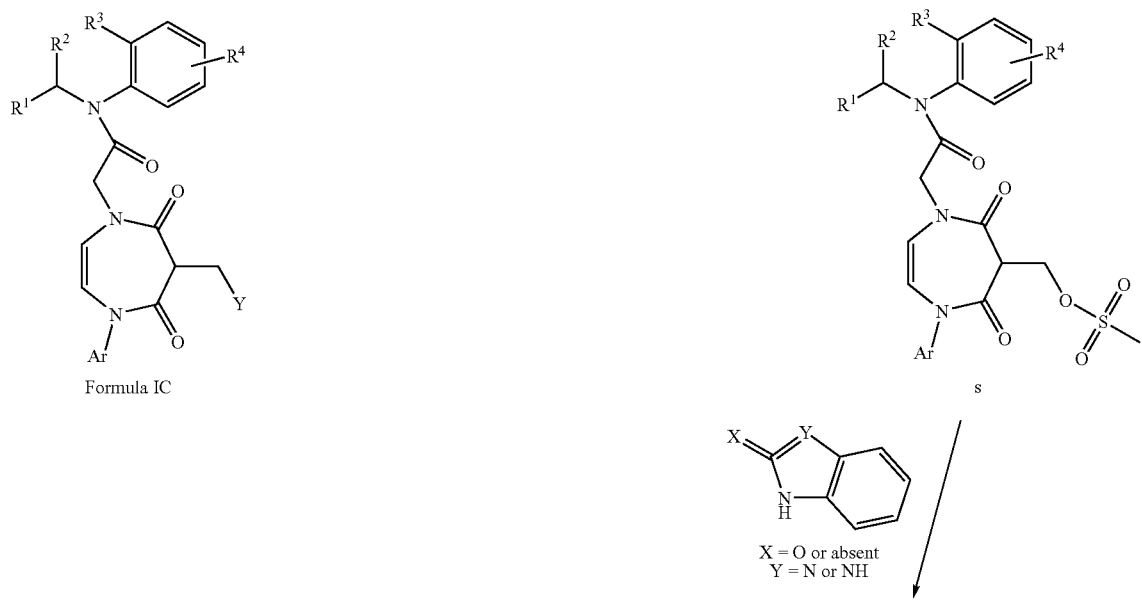
Formula IC
s
X = O or absent
Y = N or NH

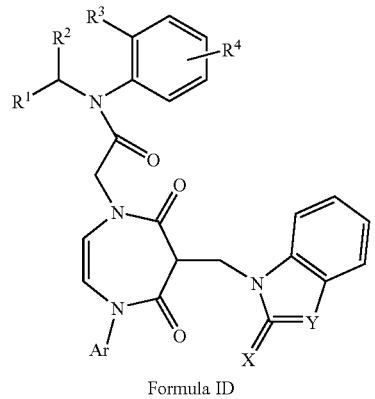

Formula ID

Fourth Preparation. Compounds of Formula 1 (specifically of Formula 1E) can be prepared in accordance with the Reaction Schematic 4 set forth below. Compounds are shown with a particular Q group but may be replaced by any other Q group. Thus, 2-bromoacetaldehyde dimethyl acetal was attached to a solid support linker by reaction with the substituted diol of formula (aa) to give acetal of formula (bb). The protecting group PG was removed by hydrolysis to give the corresponding carboxylic acid of formula (cc). The carboxylic acid of formula (cc) is then activated to give the activated compound containing the LG moiety of formula (dd). Reaction of the compound of formula (dd) with the activated solid phase support (SPS-Nu) and one or more (preferably two) amide-forming coupling agents then afforded the SPS-linked compound (ee). Reaction of the bromomethylene moiety of formula (ee) with an aryl amine (Ar—NH$_2$) yielded the disubstituted aniline of formula (ff), which, in turn was coupled with methyl malonyl chloride of formula (b) to give the methyl malonyl amide of formula (gg). The SPS-coupled compound of formula (gg) underwent selective ester hydrolysis to afford the malonic mono-amide mono-carboxylic acid (hh). Coupling of compound of formula (hh) with the N-substituted glycine derivative (f') and one or more (preferably two) amide-forming coupling agents then yielded compounds of formula (ii). Alkylation of compound of formula (ii) with the bromomethylene aryl compound of formula (h') or BrCH$_2$Y gave a compound of formula (jj). Upon treatment of compound of formula (jj) with acid, simultaneous cleavage of the SPS-linker occurs along with the deprotection of the aldehyde and amine protecting groups, followed by acid-catalyzed aldehyde and amide cyclization to give the 2,4-dioxo-1,5-diazepine compounds of Formula 1E Reaction Schematic 4

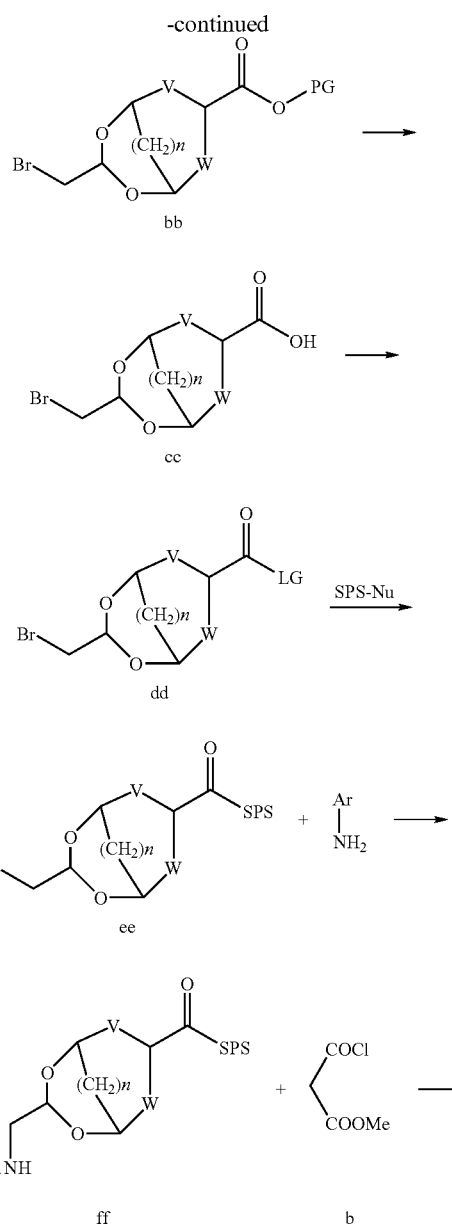

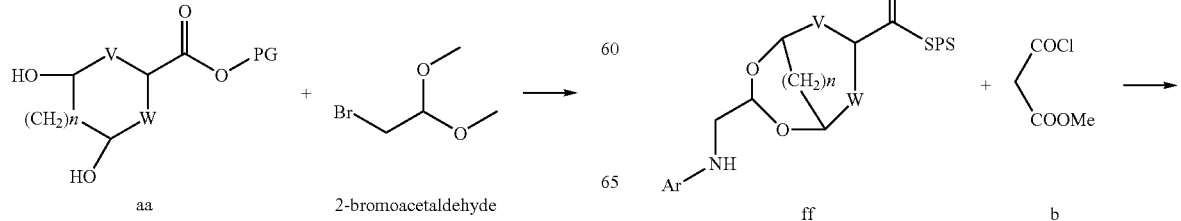

LG = leaving group
SPS = solid phase support
Nu = nucleophile
n = 0, 1, 2
W = nothing or —(CH$_2$)$_{(1-3)}$
V = nothing or —(CH$_2$)$_{(1-2)}$

EXPERIMENTAL

The following examples are intended for illustration only and are not intended to limit the scope of the invention in any way, the invention being defined by the claims.

Preparation of Example 1

2-[2,4-Dioxo-3-(1H-indazol-3-ylmethylene)-5-phenyl-2,3,4,5-tetrahydro-1H-1,5-diazepin-1-yl]-N-isopropyl-N-(4-methoxyphenyl)acetamide (Example 1)

via Reaction Scheme 1

Intermediate 1c

Methyl 3-[(N-2,2-diethoxyethyl)-N-phenyl]amino-3-oxopropanoate

A solution of methyl malonyl chloride (1b, 1.1 g) in chloroform (10 ml) was added to a solution of 2-(N-anilino)

acetaldehyde diethyl acetal (1a, 2.09 g) and pyridine (0.79 g) in chloroform (20 ml) at 0° C. The reaction mixture was stirred for 2 hrs., evaporated and the residue purified by column chromatography on silica gel (Hexane 50%: Ethyl acetate 50%), to afford the titled product (1c, 2 g). $^1$H NMR (300 MHz, CDCl$_3$): 7.38 (m, 3H); 7.26 (m, 2H), 4.82 (t, J=5.6 Hz, 1H), 3.80 (d, J=5.6 Hz, 2H), 3.67 (s, 3H), 3.60 (m, 4H), 3.20 (s, 2H), 1.16 (t, J=7 Hz, 6H), Intermediate 1d 3-[(N-2,2-Diethoxyethyl)-N-phenyl]amino-3-oxo-propanoic Acid To a solution of methyl 3-[N-(2,2-diethoxyethyl)-N-phenyl]amino-3-oxopropanoate (1c) in THF (10 ml) and water (5 ml), 1N aqueous solution of NaOH (3.5 ml) was added and resultant mixture was stirred overnight at room temperature. THF was removed in vacuo and 1N aqueous solution of NaHSO$_4$ (3.5 ml) was added. The product was extracted with ethyl acetate (2×50 ml). The organic layers were combined, dried with anhydrous MgSO$_4$ and the solvent removed in vacuo to afford 1 g of the titled product 1d. $^1$H NMR (300 MHz, CDCl$_3$) 7.38 (m, 3H), 7.26 (m, 2H), 4.82 (t, J=5.6 Hz, 1H), 3.80 (d, J=5.6 Hz, 2H), 3.67 (s, 3H), 3.60 (m, 4H), 3.20 (s, 2H), 1.16 (t, J=7 Hz, 6H), Intermediate 1f N$^1$-Isopropyl-N$^1$-(4-methoxyphenyl)glycinamide 2-Bromo-N-isopropyl-N-(4-methoxyphenyl)acetamide (1e, 2.86 g) was dissolved in methanol saturated with ammonia at 0° C. and left for 3 days at room temperature in a sealed flask. Methanol and ammonia were removed in vacuo and the residue was dissolved in chloroform (100 ml) and washed with water (2×50 ml). The organic layer was separated and dried with anhydrous MgSO$_4$ and concentrated in vacuo to afford the titled product (1f, 2.7 g). $^1$H NMR (300 MHz, CDCl$_3$) 6.96 (m, 4H), 4.99 (sept., J=6.6 Hz, 1H), 3.84 (s, 3H), 2.97 (s, 2H), 1.58 (s, 2H), 1.05 (d, J=6.6 Hz, 6H), Intermediate 1 g N-(2,2-Diethoxyethyl)-N-phenylamino 2-[N'-Isopropyl-(N'-4-methoxyphenylamino)-2-oxoethyl]Malonamide A solution of N$^1$-isopropyl-N$^1$-(4-methoxyphenyl)glycinamide (1f, 0.7 g), intermediate (1d, 0.53 g) and HOBT coupling agent (0.31 g) in DMF (5 ml) was cooled to 0° C. and EDC coupling agent (0.47 g) was added in one portion. The reaction mixture was stirred overnight and poured into ice water and were extracted with ethyl acetate (3×15 ml). The combined organic layers were dried with anhydrous MgSO$_4$, concentrated in vacuo and purified by column chromatography on silica gel (1% MeOH: 99% CHCl$_3$), providing 900 mg of the titled compound 1 g. $^1$H NMR (300 MHz, CDCl$_3$) 8.21 (m, 1H), 7.28 (m, 6H), 6.99 (m, 2H), 6.88 (m, 2H), 4.95 (sept., J=7 Hz, 1H), 4.80 (t, J=5.6 Hz, 1H), 3.81 (s, 3H), 3.78 (m, 2H), 3.54 (m, 6H), 3.03 (s, 2H), 1.13 (t, J=7 Hz, 6H), 1.03 (d, J=7 Hz, 6H), Intermediate 1i N-(2,2-Diethoxyethyl)-N-phenylamino 2-[N$^1$-Isopropyl-(N'-4-methoxyphenylamino)-2-oxoethyl]-2-(1-tert-butyloxycarbonyl-1H-indazol-3-ylmethylene)malonamide To a solution of N-(2,2-diethoxyethyl)-N-phenylamino 2-[N'-isopropyl-(N'-4-methoxyphenylamino)-2-oxoethyl] malonamide (1 g, 680 mg) in dry DMF (5 ml), 0.5M solution of potassium bis(trimethylsilyl)amide in toluene (2.74 ml) was added at 0° C. The reaction mixture was stirred for 30 min. at 0° C. and a solution of tert-butyl 3-(bromomethylene)-1H-indazole-1-carboxylate (1 h) (423 mg) in dry DMF (2 ml) was added dropwise. The reaction mixture was stirred overnight at room temperature, poured into water and this mixture was extracted with ethyl acetate (2×15 ml). The organic phase was separated and dried. The solvent was removed in vacuo and the residue was purified by column chromatography on silica gel (MeOH 1%: CHCl$_3$ 99%) to afford the titled product (1i, 700 mg). $^1$H NMR (400 MHz, CDCl$_3$) 8.05 (d, J=8 Hz, 1H), 7.64 (d, J=8 Hz, 1H), 7.46 (m, 1H), 7.12 (m, 11H), 4.95 (sept., J=7 Hz, 1H), 4.60 (t, J=5.6 Hz, 1H), 3.88 (m, 1H), 3.81 (s, 3H), 3.68 (m, 3H), 3.52 (m, 5H), 3.24 (m, 2H), 1.70 (s, 9H), 1.03 (m, 12H), 2-[2,4-Dioxo-3-(1H-indazol-3-ylmethylene)-5-phenyl-2,3,4,5-tetrahydro-1H-1,5-diazepin-1-yl]-N-isopropyl-N-(4-methoxyphenyl)acetamide (Example 1)

A solution of N-(2,2-diethoxyethyl)-N-phenylamino 2-[N'-isopropyl-(N'-4-methoxyphenylamino)-2-oxoethyl]2-(1-tert-butyloxycarbonyl-1H-indazol-3-ylmethylene)malonamide (1i, 200 mg) and p-toluenesulfonic acid (anhydrous, 20 mg) in dry toluene (80 ml) was placed in an oil bath at 70° C. and stirred for 30 min. Toluene was removed in vacuo and the residue was purified by column chromatography on silica gel (Hexane 50%:Ethyl acetate 50%) to afford the partially deprotected cyclic product 2-[2,4-dioxo-3-(1-tert-butyloxycarbonyl-1H-indazol-3-ylmethylene)-5-phenyl-2,3,4,5-tetrahydro-1H-1,5-diazepin-1-yl]-N-isopropyl-N-(4-methoxyphenyl)acetamide (170 mg). $^1$H NMR (400 MHz, CDCl$_3$) 8.03 (d, J=8.4 Hz, 1H). 7.85 (d, J=8 Hz, 1H), 7.47 (t, J=7.7 Hz, 1H), 7.31 (m, 6H), 7.11 (m, 2H), 6.93 (m, 2H), 6.00 (s, 2H), 4.95 (sept., J=6.7 Hz, 1H), 4.35 (d-d, J=8.9 Hz, J=4.8 Hz, 1H), 3.93 (m, 2H), 3.85 (d-d, J=16.6 Hz, 8.9 Hz, 1H), 3.82 (s, 3H), 3.58 (d-d, J=16.6 Hz, J=4.8 Hz, 1H), 1.65 (s, 9H), 1.04 (d, J=6.7 Hz, 6H).

The 2-[2,4-dioxo-3-(1-tert-butyloxycarbonyl-1H-indazol-3-ylmethylene)-5-phenyl-2,3,4,5-tetrahydro-1H-1,5-diazepin-1-yl]-N-isopropyl-N-(4-methoxyphenyl)acetamide (170 mg) was dissolved in CHCl$_3$ (10 ml) and TFA (5 ml) was added. The reaction mixture was stirred for 6 hrs and the solvents were removed in vacuo. The crude product was purified by RP HPLC Dynamax (C-8) (10 ml/min (50% Acetonitrile, 50% Water (0.1% TFA), followed by lyophilization, to afford the titled product of Example 1 (135 mg) as a white lyophilate. HPLC Column: Dynamax C-8 2 ml/min., 30-70% Acetonitrile in aqueous TFA (0.1% v/v) over 20 min., T$_r$=17.1 min. $^1$H NMR (400 MHz, CDCl$_3$) 7.93 (d, J=8.3 Hz, 1H), 7.59 (m, 2H), 7.11 (m, 2H), 7.31 (m, 6H), 6.93 (m, 2H), 6.00 (s, 2H), 4.92 (sept., J=6.3 Hz, 1H), 4.15 (m, 1H), 3.92 (m, 4H), 3.82 (s, 3H), 1.04 (d, J=6.3 Hz, 6H), MS (FAB) [M+H]$^+$=538.

Preparation of Example 2 (Enantiomer II)

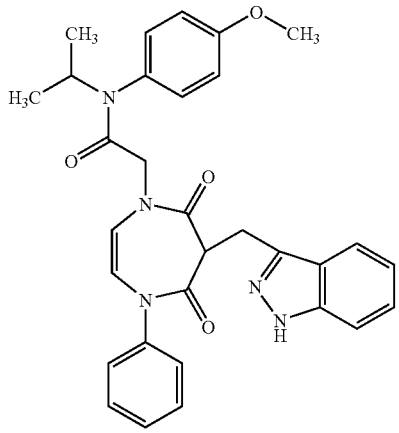

(S or R)(2-[2,4-Dioxo-3-(1H-indazol-3-ylmethylene)-5-phenyl-2,3,4,5-tetrahydro-1H-1,5-diazepin-1-yl]-N-isopropyl-N-(4-methoxyphenyl)acetamide (Example 2)

Enantiomer #2 of Example 1

Racemic compound of Example 1 was separated on the Prochrom Preparative Supercritical Fluid Chromatograph Super C20
Column Chiralcel OD (2×25CM)
Temperature: 40 C
Pressure: 21 MPa
CO2 flow rate: 50 g/min
Mobile Phase Methanol with 10% Chloroform at a flow rate of 16 ml/min
300 nm
75 mg per injection
>90% recovery
Enantiomer #1:4.0 min
Enantiomer #2:7.2 min (Example 2)

Preparation of Example 3

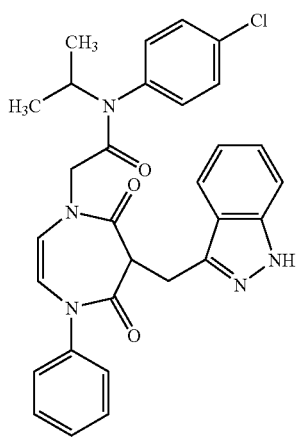

2-[2,4-dioxo-3-(1H-indazol-3-ylmethylene)-5-phenyl-2,3,4,5-tetrahydro-1H-1,5-diazepin-1-yl]-N-(4-chlorophenyl)-N-isopropylacetamide Hydrochloride Salt (Example 3)

via Reaction Scheme 2

Intermediate 3j

N-(2,2-Diethoxyethyl)-N-phenyl Malonamide

Sodium cyanide (1.50 g) was added to a solution of methyl 3-[(N-2,2-diethoxyethyl)-N-phenyl]amino-3-oxopropanoate (1c, 66.65 g) in 7M methanolic ammonia (1.5 L) and the mixture was stirred at ambient temperature in a stoppered flask for approximately 64 hours. The reaction mixture was evaporated in vacuo and the residue was partitioned between $CH_2Cl_2$ and water. After separation, the aqueous layer was extracted twice with $CH_2Cl_2$. The combined organic layers were washed with saturated aqueous brine, dried over anhydrous $MgSO_4$, filtered and the filtrate evaporated in vacuo. The residue was purified on flash grade silica gel eluting with 75-100% ethyl acetate in hexane. Fractions containing the product were combined, evaporated in vacuo and dried under high vacuum to provide N-(2,2-diethoxyethyl)-N-phenyl malonamide (3j, 60.88 g) as an oil. $^1$H NMR (300 MHz, $CDCl_3$) 1.19 (t, J=7 Hz, 6H), 3.10 (s, 2H), 3.60 (m, 4H), 3.85 (d, J=6 Hz, 2H), 4.80 (t, J=6 Hz, 1H), 5.76 (s, 1H), 7.25 (d, J=7 Hz, 2H), 7.41 (m, 3H), 7.73 (s, 1H). MS (ESI) $[M+Na]^+$=317

Intermediate 3k

N-(2,2-Diethoxyethyl)-N-phenylamino 2-(1-tert-butyloxycarbonyl-1H-indazol-3-ylmethylene)malonamide A solution of HMDS (39.6 mL, 19.8 mmol, 0.5 M in THF) was injected into a 0°C solution of the N-(2,2-diethoxyethyl)-N-phenyl malonamide (3j, 5.3 g, 18.0 mmol) and anhydrous DMF (90 mL) under a nitrogen atmosphere. To the stirred reaction mixture, a solution of the tert-butyl 3-(bromomethylene)-1H-indazole-1-carboxylate (1 h, 5.6 g, 18.0 mmol) and anhydrous DMF (20 mL) was transferred by canula over a span of 30 mins. After the addition of the bromide 1 h, the ice bath was removed and the reaction was allowed to warm to ambient temperature. The reaction stirred at room temperature for 90 mins. The solvent was removed under vacuum while heating to 60° C. The residue was dissolved in ethyl acetate, washed with distilled water, 10% aqueous sodium hydrogen sulfate, saturated sodium bicarbonate and brine. The organic fraction was dried over anhydrous sodium sulfate and purified by silica gel column chromatography (gradient: 50 to 100% ethyl acetate/hexanes). Purification yielded 5.5 g of the title compound (3k). $R_f$=0.1 (1:1 Hexanes/ethyl acetate). $^1$H NMR (400 MHz, $CDCl_3$) 8.03 (d, 1H), 7.56 (d, 1H), 7.46 (t, 1H), 7.30-7.10 (m, 6H), 6.68 (br.s, 1H), 5.26 (br.s, 1H), 4.65 (t, 1H), 3.97 (dd, 1H), 3.88 (dd, 1H), 3.67 (dd, 1H), 3.60-3.40 (m, 4H), 3.40-3.30 (m, 2H), 1.68 (s, 9H), 1.08 (dt, 6H).

Intermediate 3

3-(1-tert-Butyloxycarbonyl-1H-indazol-3-ylmethylene)-5-phenyl-1H-1,5-diazepine-2,4-dione A solution of anhydrous para-toluenesulfonic acid (13 mL, 2.6 mmol, 0.2M in toluene), was injected into a stirred solution of N-(2,2-diethoxyethyl)-N-phenylamino 2-(1-tert-butyloxycarbonyl-1H-indazol-3-ylmethylene)malonamide (3k, 5.55 g, 10.3 mmol) in toluene (200 mL) under a nitrogen atmosphere. The reaction was heated to 60° C. and stirred for 60 mins. The yellow suspension was concentrated under vacuum to a brown oil. The crude product was purified by crystallization from a warm mixture of methylene chloride and hexanes. The off-white crystals were collected by filtration to yield 2.4 g of the title compound (3l). $R_f$=0.2 (1:1 Hexanes/ethyl acetate). $^1$H NMR (400 MHz, DMSO-$d_6$) 9.95 (d, 1H), 8.00 (d, 1H), 7.92 (d, 1H), 7.57 (t, 1H), 7.45-7.1 (m, 5H), 7.05 (d, 1H), 6.13 (m, 1H), 6.06 (m, 1H), 4.01 (m, 1H), 2.23 (s, 2H), 1.56 (s, 9H). MS (ESI): M+H=433.

N-(4-Chlorophenyl)-2-[2,4-dioxo-3-(1H-indazol-3-ylmethylene)-5-phenyl-2,3,4,5-tetrahydro-1H-1,5-diazepin-1-yl]-N-isopropylacetamide Hydrochloride Salt (Example 3)

NaHMDS (0.345 mL, 0.21 mmol, 0.6 M in THF) was injected into a 0° C. solution of 3-(1-tert-butyloxycarbonyl-1H-indazol-3-ylmethylene)-5-phenyl-1H-1,5-diazepine-2,4-dione (3l, 81 mg, 0.19 mmol) in anhydrous DMF (2 mL) and stirred for 15 mins under a nitrogen atmosphere. A solution 2-bromo-N-(4-chlorophenyl)-N-isopropylacetamide (3e, 60 mg, 0.21 mmol), dissolved in anhydrous DMF (1 mL), was transferred to the reaction through a canula. The ice bath was removed and the reaction was allowed to warm to room temperature. The reaction stirred at room temperature for 18 hrs. The reaction was concentrated under vacuum at 60° C. to a residue. The crude residue was dissolved in ethyl acetate, washed with 10% aqueous sodium hydrogen sulfate, saturated aqueous sodium bicarbonate and brine. The organic solution was then dried over anhydrous sodium sulfate and concentrated under vacuum. The crude product was purified by silica gel chromatography (gradient: 30% to 50% ethyl acetate/hexanes). $R_f$=0.3 (1:1 Hexanes/ethyl acetate). $^1$H NMR (400 MHz, CDCl$_3$) 8.00 (d, 1H), 7.83 (d, 1H), 7.45 (t, 1H), 7.40 (d, 2H), 7.35-7.20 (m, 6H), 7.13 (br.d, 2H), 5.98 (q, 2H), 4.94 (sept, 1H), 4.33 (q, 1H), 3.93 (d, 1H), 3.85 (t, 1H), 3.81 (m, 1H), 3.55 (dd, 1H), 1.63 (s, 9H), 1.02 (d, 6H).

The 2-[2,4-dioxo-3-(1H-indazol-3-ylmethylene)-5-phenyl-2,3,4,5-tetrahydro-1H-1,5-diazepin-1-yl]-N-(4-chlorophenyl)-N-isopropylacetamide obtained in the previous step was dissolved in 4N HCl/dioxane and stirred at room temperature for 3 hrs. The solvent was removed under vacuum and the residue was lyophilized directly (acetonitrile/water) to yield 50 mg of the title compound N-(4-chlorophenyl)-2-[2,4-dioxo-3-(1H-indazol-3-ylmethylene)-5-phenyl-2,3,4,5-tetrahydro-1H-1,5-diazepin-1-yl]-N-isopropylacetamide hydrochloride salt (Example 3). $^1$H NMR (400 MHz, DMSO-$d_6$) 7.73 (d, 1H), 7.53 (d, 2H), 7.38 (t, 3H), 7.33-7.15 (m, 7H), 7.45-7.15 (m, 5H), 7.03 (t, 1H), 6.14 (s, 2H), 4.73 (sept, 1H), 4.11 (t, 1H), 3.95 (d, 1H), 3.75 (d, 1H) 3.60-3.30 (2H). MS (ESI): M+H=542.

Preparation of Example 4

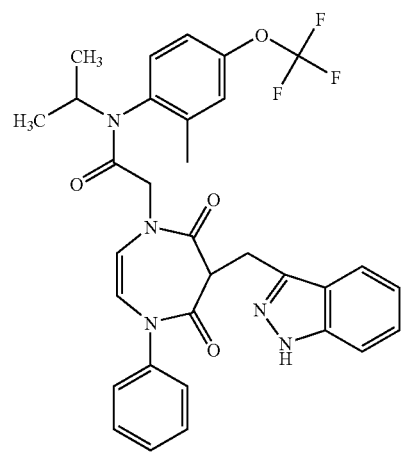

2-[2,4-Dioxo-3-(1H-indazol-3-ylmethylene)-5-phenyl-2,3,4,5-tetrahydro-1H-1,5-diazepin-1-yl]-N-isopropyl-N-(2-methyl-4-trifluoromethoxy)phenyl)acetamide (Example 4)

Synthesized via Reaction Scheme 1.

I $^1$H NMR (400 MHz, CD$_3$OD) 7.91 (1H, d, J=8.06 Hz), 7.35 (10H, m), 7.21 (1H, m), 7.09 (1H, dd, J=7.51 Hz), 6.11 (2H, m), 4.69 (1H, qq, J=6.59 Hz), 4.22 (1H, m), 4.07 (2H, m), 3.71 (2H, m), 3.56 (1H, m), 2.39 (3H, d, J=4.03 Hz), 1.99 (3H, s), 1.22 (6H, m). MS (EI) [M+H]$^+$=606.

Preparation of Example 5

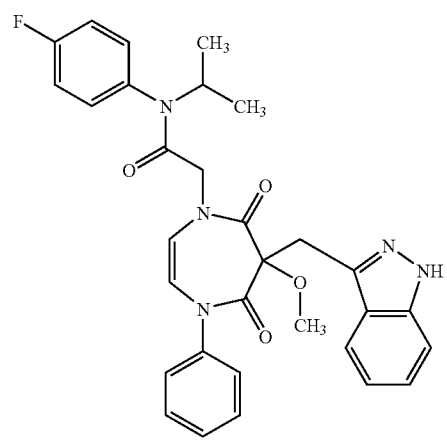

2-[2,4-Dioxo-3-(1H-indazol-3-ylmethylene)-3-methoxy-5-phenyl-2,3,4,5-tetrahydro-1H-1,5-diazepin-1-yl]-N-(4-fluorophenyl) N-isopropylacetamide (Example 5)

Synthesized via Reaction Scheme 1.

$^1$H NMR (400 MHz, CDCl$_3$) 7.96 (d, J=8.4 Hz, 1H); 7.49-7.58 (m, 2H); 7.32-7.36 (m, 2H); 7.15-7.28 (m, 8H); 5.95 (d,

J=6.6 Hz, 1H); 6.92 (d, J=6.6 Hz, 1H); 4.98 (q, J=7.2 Hz, 1H); 4.04-4.21 (m, 3H); 3.74 (d, J=6.6 Hz, 1H); 3.47 (s, 3H); 1.07 (m, 6H) MS (FAB) [M+H]⁺=556.

Preparation of Example 6

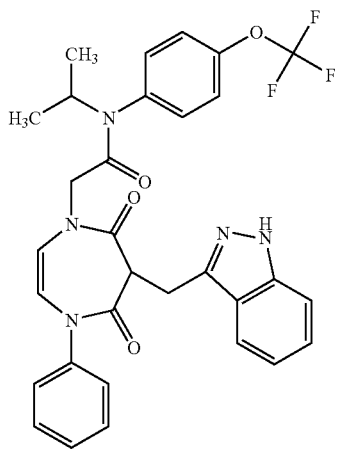

2-[2,4-Dioxo-3-(1H-indazol-3-ylmethylene)-5-phenyl-2,3,4,5-tetrahydro-1H-1,5-diazepin-1-yl]-N-isopropyl-N-(4-(trifluoromethoxyphenyl) acetamide (Example 6)

Synthesized via Reaction Scheme 1.
$R_f$=0.1 (1:1 Hexanes/ethyl acetate). ¹H NMR (300 MHz, CDCl₃) 7.80 (d, 1H), 7.40-7.15 (12H), 7.10 (t, 1H), 5.98 (m, 2H), 4.95 (sept, 1H) 4.20 (m, 1H), 3.95-3.70 (3H), 3.60 (m, 1H), 1.01 (d, 6H). MS (ESI): M+H=592.

Preparation of Example 7

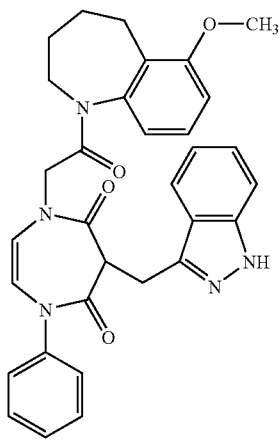

3-(1H-Indazol-3-ylmethylene)-1-[2-(6-methoxy-2,3,4,5-tetrahydro-1H-1-benzazepin-1-yl)-2-oxoethyl]-5-phenyl-1H-1,5-diazepine-2,4-dione (Example 7)

Synthesized via Reaction Scheme 1.
$R_f$=0.3 (1:1 Hexanes/ethyl acetate). ¹H NMR (300 MHz, CDCl₃) 7.96 (t, 1H), 7.57 (t, 2H), 7.45-7.15 (7H), 6.95-6.80 (m, 2H), 6.20-6.05 (2H), 5.45 (br. s, 1H) 4.66 (m, 1H), 4.43-4.18 (3H), 3.88 (s, 3H), 4.04-3.80 (2H), 3.43 (m, 1H), 2.73 (t, 1H), 2.42 (q, 1H), 1.98 (m, 2H), 1.81 (m, 1H), 1.33 (d, 1H). MS (ESI): M+H=550.

Preparation of Example 8

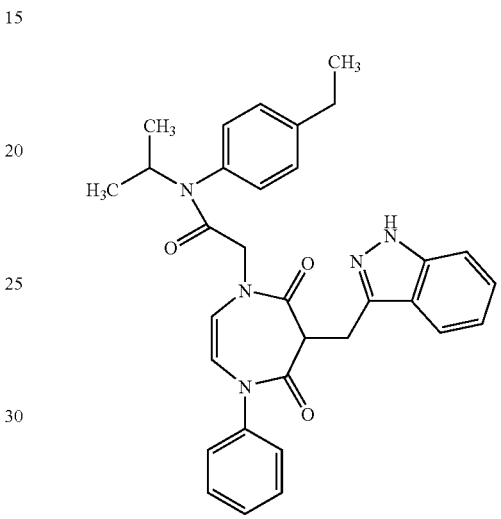

2-[2,4-Dioxo-3-(1H-indazol-3-ylmethylene)-5-phenyl-2,3,4,5-tetrahydro-1H-1,5-diazepin-1-yl]-N-(4-ethylphenyl)-N-isopropylacetamide (Example 8)

Synthesized via Reaction Scheme 1.
$R_f$=0.1 (1:1 Hexanes/ethyl acetate). ¹H NMR (400 MHz, CDCl₃) 7.75 (d, 1H), 7.40-7.15 (9H), 7.15-7.00 (3H), 5.99 (d, 1H), 5.89 (d, 1H), 4.95 (sept, 1H) 4.20 (m, 1H), 4.00 (d, 1H), 3.82 (d, 1H), 3.78 (d, 1H), 3.48 (dd, 1H), 2.60 (q, 2H), 1.20 (t, 3H), 1.01 (d, 6H). MS (ESI): M+H=536.

Preparation of Example 9

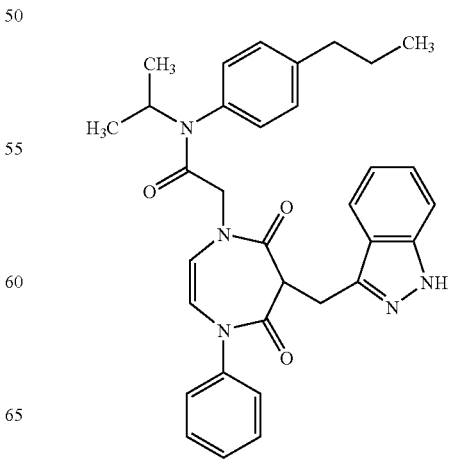

2-[2,4-Dioxo-3-(1H-indazol-3-ylmethylene)-5-phenyl-2,3,4,5-tetrahydro-1H-1,5-diazepin-1-yl]-N-isopropyl-N-(4-propylphenyl)acetamide (Example 9)

Synthesized via Reaction Scheme 2.

$^1$H NMR (400 MHz, DMSO-$d_6$) 12.59 (s, 1H), 7.79 (d, 1H), 7.43 (m, 3H), 7.41-7.25 (6H), 7.20 (br. s, 2H), 7.09 (t, 1H) 6.19 (q, 2H) 4.78 (sept, 1H), 4.16 (t, 1H), 3.89 (dd, 2H), 3.48 (dq, 2H), 2.60 (t, 2H), 1.62 (q, 2H), 1.00 (d, 6H), 0.90 (t, 3H). MS (ESI): M+H=550.

Preparation of Example 10

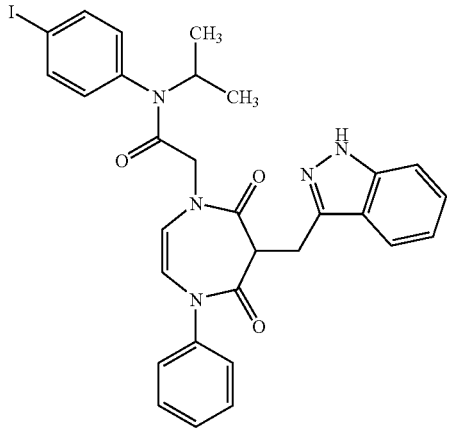

2-[2,4-Dioxo-3-(1H-indazol-3-ylmethylene)-5-phenyl-2,3,4,5-tetrahydro-1H-1,5-diazepin-1-yl]-N-(4-iodophenyl)-N-isopropylacetamide (Example 10)

Synthesized via Reaction Scheme 2.

$^1$H NMR (400 MHz, DMSO-$d_6$) 12.55 (s, 1H), 7.84 (d, 2H), 7.80 (d, 1H), 7.41 (m, 3H), 7.32 (m, 4H), 7.10 (m, 3H) 6.19 (s, 2H), 4.75 (sept, 1H), 4.15 (m, 1H), 4.02 (d, 1H), 3.80 (d, 1H), 3.71 (m, 1H), 3.65-3.30 (1H), 1.00 (d, 6H). MS (ESI): M+H=634.

Preparation of Example 11

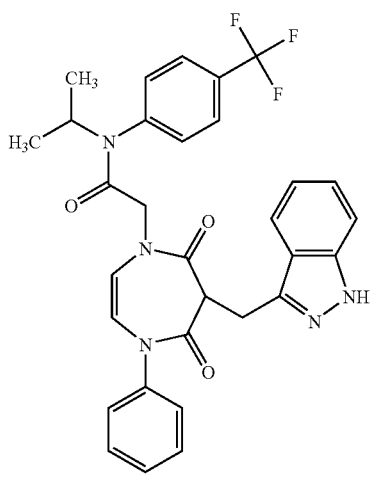

2-[2,4-Dioxo-3-(1H-indazol-3-ylmethylene)-5-phenyl-2,3,4,5-tetrahydro-1H-1,5-diazepin-1-yl]-N-isopropyl-N-(4-trifluoromethylphenyl)acetamide (Example 11)

Synthesized via Scheme 2.

$^1$H NMR (400 MHz, DMSO-$d_6$) 12.60 (s, 1H), 7.89 (d, 2H), 7.78 (d, 1H), 7.56 (s, 2H), 7.43 (m, 3H), 7.40-7.25 (m, 4H), 7.08 (t, 1H), 6.19 (s, 2H), 4.80 (sept, 1H), 4.16 (t, 1H), 3.90 (dd, 2H), 3.46 (dq, 2H), 1.00 (d, 6H). MS (ESI): M+H=576.

Preparation of Example 12

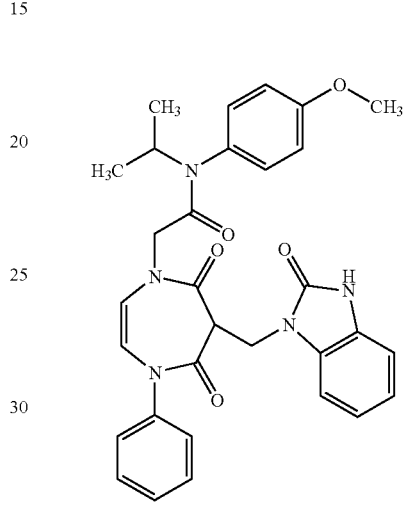

2-[2,4-Dioxo-3-(2,3-dihydro-2-oxo-1H-benzimidazol-1-yl)methylene-5-phenyl-2,3,4,5-tetrahydro-1H-1,5-diazepin-1-yl]-N-isopropyl-N-(4-methoxyphenyl)acetamide (Example 12)

via Reaction Scheme 3

Intermediate 12m

N-(2,2-Diethoxyethyl)-N-phenyl Malonamide 2-(1,3-Trimethylene)dithioketal

A mixture of N-(2,2-diethoxyethyl)-N-phenyl malonamide (3j, 27.80 g), trimethylene dithiotosylate (39.39 g) and anhydrous potassium carbonate (26.14 g) was combined in DMF (200 mL) and stirred under a nitrogen atmosphere at ambient temperature for approximately 64 hours. DMF was removed in vacuo and the residue was triturated with water. The resulting slurry was filtered and the wet cake was slurried in Et$_2$O, filtered and dried under high vacuum to provide N-(2,2-diethoxyethyl)-N-phenyl malonamide 2-(1,3-trimethylene)dithioketal (12m, 21.75 g) as a solid. The aqueous mother liquor was extracted with ethyl acetate, diluted with saturated brine and extracted again with ethyl acetate. The combined organic layers were dried over anhydrous MgSO$_4$, filtered and evaporated in vacuo to a residue. The Et$_2$O mother liquor was evaporated in vacuo and the residue was partitioned between CH$_2$Cl$_2$ and water. The organic layer was dried over anhydrous MgSO$_4$, filtered and evaporated in vacuo to a residue. The two organic residues were dissolved in 1:1 ethyl acetate/hexane (100 mL) and seeded. The resulting slurry was stirred overnight, filtered and dried under high vacuum to provide an additional crop of the title compound (12m, 7.27 g). $^1$H NMR (400 MHz, CDCl$_3$) 1.15 (t, J=7 Hz, 6H), 1.93 (m, 2H), 2.91 (m, 4H), 3.52 (m, 2H), 3.61 (m, 2H), 3.76 (b, 2H), 4.81 (b, 1H), 5.06 (s, 1H), 6.19 (s, 1H), 7.31 (m, 5H).

MS (ESI) [M+Na]+=421

Intermediate 12n

5-Phenyl-1H-1,5-diazepine-2,4-dione 3-(1,3-Trimethylene)dithioketal

N-(2,2-Diethoxyethyl)-N-phenyl malonamide 2-(1,3-trimethylene)dithioketal (12m, 15.00 g) and benzenesulphonic acid (0.596 g) were combined in toluene (1 L) under nitrogen and heated to 70° C. for 45 min. After cooling to room temperature, the toluene was removed in vacuo and the residue was partitioned between CH$_2$Cl$_2$ and 0.1 N NaOH. The organic layer was separated and the aqueous layer was back-extracted twice with CH$_2$Cl$_2$. The combined organic layers were dried over anhydrous MgSO$_4$, filtered, evaporated in vacuo and crystallized from a minimum quantity of CH$_2$Cl$_2$. Filtration and drying under high vacuum provided 5-phenyl-1H-1,5-diazepine-2,4-dione 3-(1,3-trimethylene)dithioketal (12n 3.55 g) as a solid. The CH$_2$Cl$_2$ mother liquor was evaporated in vacuo and a second crop was crystallized from ethyl acetate, filtered and dried under high vacuum to provide an additional crop (2.56 g) of the title compound (12n). $^1$H NMR (400 MHz, CDCl$_3$) 1.99 (m, 2H), 3.00 (m, 4H), 5.80 (m, 2H), 7.31 (m, 6H).

MS (ESI) [M+Na]$^+$=329

Intermediate 12o 2-(2,4-Dioxo-5-phenyl-2,3,4,5-tetrahydro-1H-1,5-diazepin-1-yl)-N-isopropyl-N-(4-methoxyphenyl) acetamide 3-(1,3-Trimethylene)dithioketal A solution of 5-phenyl-1H-1,5-diazepine-2,4-dione 3-(1, 3-trimethylene)dithioketal (12n, 6.017 g) in anhydrous DMF (40 mL) under nitrogen was cooled to 0-50 C. Sodium bis (trimethylsilyl)amide (0.6 M in toluene, 34.4 mL) was added via syringe to the reaction mixture. A solution of 2-bromo-N-isopropyl-N-(4-methoxyphenyl)acetamide (1e, 5.908 g) in anhydrous DMF (5 mL) was added to the reaction mixture via pipette. After 25 min., the reaction mixture was quenched with glacial acetic acid and evaporated in vacuo. The residue was partitioned between 1N NaHSO$_4$ and ethyl acetate. The layers were separated and the aqueous layer was back-extracted three times with ethyl acetate. The combined organic layers were dried over anhydrous MgSO$_4$, filtered and evaporated in vacuo. The residue was purified on flash grade silica gel eluting with 40-60% ethyl acetate in hexanes. Fractions containing the product were combined, evaporated in vacuo and dried under high vacuum to provide the title compound as a foam (12o, 9.753 g). $^1$H NMR (400 MHz, CDCl$_3$) 1.03 (d, J=7 Hz, 6H), 1.96 (m, 2H), 2.92 (b, 2H), 3.18 (b, 2H), 3.66 (b, 1H), 3.80 (s, 3H), 4.10 (b, 1H), 4.94 (sept., J=7 Hz, 1H), 5.75 (d, J=7 Hz, 1H), 5.80 (d, J=7 Hz, 1H), 6.91 (m, 2H), 7.13 (b, 2H), 7.20 (m, 2H), 7.26 (m, 1H), 7.35 (m, 2H).

MS (ESI) [M+H]$^+$=512

Intermediate 12p 2-(2,4-Dioxo-5-phenyl-2,3,4,5-tetrahydro-1H-1,5-diazepin-1-yl)-N-isopropyl-N-(4-methoxyphenyl) acetamide A solution of 2-(2,4-dioxo-5-phenyl-2,3,4,5-tetrahydro-1H-1,5-diazepin-1-yl)-N-isopropyl-N-(4-methoxyphenyl) acetamide 3-(1,3-trimethylene)dithioketal (12o, 7.00 g) and NiCl$_2$ (7.16 g) in 3:1 methanol/THF (40 mL) was cooled under argon to 0-5° C. The reaction mixture was treated with sodium borohydride (3.11 g) in portions. Additional NiCl$_2$ (3.58 g) was added followed by additional sodium borohydride (1.50 g) in portions. The reaction mixture was filtered washing with ethyl acetate and hot methanol. The filtrate was evaporated in vacuo and the residue was partitioned between aqueous 1N NaHSO$_4$ and CH$_2$Cl$_2$. After separating the layers, the aqueous layer was back-extracted twice with CH$_2$Cl$_2$. The combined organic layers were dried over anhydrous MgSO$_4$, filtered and evaporated in vacuo. The residue was triturated with diethyl ether, filtered and dried under high vacuum to provide 2-(2,4-dioxo-5-phenyl-2,3,4,5-tetrahydro-1H-1,5-diazepin-1-yl)-N-isopropyl-N-(4-methoxyphenyl)acetamide (12p, 3.521 g) as a solid. The ether mother liquor was evaporated in vacuo and the residue was triturated again with diethyl ether. The slurry was filtered and the solid dried under high vacuum to provide a second crop of the title compound (12p, 0.103 g). $^1$H NMR (400 MHz, CDCl$_3$) 1.03 (d, J=7 Hz, 6H), 3.62 (s, 2H), 3.80 (s, 3H), 3.88 (s, 2H), 4.92 (sept. 7 Hz, 1H), 5.84 (d, J=7 Hz, 1H), 5.95 (d, J=7 Hz, 1H), 6.91 (m, 2H), 7.10 (m, 2H), 7.25 (m, 3H), 7.35 (m, 2H).

MS (ESI) [M+H]$^+$=408

Intermediate 12q

2-[2,4-Dioxo-5-phenyl-3-[2-(trimethylsilyloxy)-1-ethoxymethylene]-2,3,4,5-tetrahydro-1H-1,5-diazepin-1-yl]-N-isopropyl-N-(4-methoxyphenyl)acetamide A solution of 2-(2,4-dioxo-5-phenyl-2,3,4,5-tetrahydro-1H-1,5-diazepin-1-yl)-N-isopropyl-N-(4-methoxyphenyl) acetamide (12p, 1.500 g) in anhydrous DMF (15 mL) under argon was cooled to 0-5° C. Sodium bis(trimethylsilyl)amide (0.6 M in toluene, 7.68 mL) was added via syringe followed 5 minutes later by chloromethyl 2-(trimethylsilyloxy)-1-ethyl ether (0.815 mL). After approximately 10 min., the reaction was quenched with glacial acetic acid and evaporated in vacuo. The residue was partitioned between ethyl acetate and water. The layers were separated and the aqueous layer was back-extracted twice with ethyl acetate. The combined organic layers were dried over anhydrous MgSO$_4$, filtered and evaporated in vacuo. The crude product was purified on flash grade silica gel eluting with 2:5 ethyl acetate/hexane. Fractions containing the product were combined, evaporated in vacuo and dried under high vacuum to provide 2-[2,4-dioxo-5-phenyl-3-[2-(trimethylsilyloxy)-1-ethoxymethylene]-2,3,4,5-tetrahydro-1H-1,5-diazepin-1-yl]-N-(4-methoxyphenyl)acetamide(12q, 1.236 g) as a foam. $^1$H NMR (400 MHz, CDCl$_3$) 0.00 (s, 9H), 0.95 (m, 2H), 1.04 (d, J=6 Hz, 3H), 1.06 (d, J=6 Hz, 3H), 3.62 (m, 3H), 3.83 (s, 3H), 3.91 (d, J=2 Hz, 2H), 4.02 (dd, J=5,10Hz, 1H), 4.15 (dd, J=8,10Hz, 1H), 4.95 (m, 1H), 5.93 (d, J=6 Hz, 1H), 5.99 (d, J=6 Hz, 1H), 6.94 (m, 2H), 7.11 (m, 2H), 7.33 (m, 5H).

MS (ESI) [M+Na]+=560.

Intermediate 12r

2-[2,4-dioxo-3-(hydroxymethylene)-5-phenyl-2,3,4,5-tetrahydro-1H-1,5-diazepin-1-yl]-N-isopropyl-N-(4-methoxyphenyl)acetamide 2-[2,4-Dioxo-5-phenyl-3-[2-(trimethylsilyloxy)-1-ethoxymethylene]-2,3,4,5-tetrahydro-1H-1,5-diazepin-1-yl]-N-isopropyl-N-(4-methoxyphenyl)acetamide (12q) was combined with trifluoroacetic acid (10 mL) under argon and cooled to 0-5° C. After approximately 20 min., the reaction mixture was evaporated in vacuo. The residue was triturated with diethyl ether and hexane, filtered and dried under high vacuum to provide 2-[2,4-dioxo-3-(hydroxymethylene)-5-phenyl-2,3,4,5-tetrahydro-1H-1,5-diazepin-1-yl]-N-isopropyl-N-(4-methoxyphenyl)acetamide (12r, 0.927 g) as a solid. $^1$H NMR (400 MHz, CDCl$_3$) 0.91 (d, J=2, 3H), 0.92 (d, J=2, 3H), 3.63 (m, 1H), 3.80 (s, 3H), 3.81 (d, J=17 Hz, 1H), 3.96 (d, J=17 Hz, 1H), 4.17 (dd, J=7, 12 Hz, 1H), 4.29 (dd, J=7, 12 Hz; 1H), 4.92 (m, 1H), 5.89 (d, J=6 Hz, 1H), 5.95 (d, J=6 Hz, 1H), 6.92 (m, 2H), 7.09 (m, 2H), 7.27 (m, 3H), 7.37 (m, 2H). MS (ESI) [M+Na]$^+$=460

Intermediate 12s

2-[2,4-dioxo-3-(methanesulfonyloxymethylene)-5-phenyl-2,3,4,5-tetrahydro-1H-1,5-diazepin-1-yl]-N-isopropyl-N-(4-methoxyphenyl)acetamide A solution of 2-[2,4-dioxo-3-(hydroxymethylene)-5-phenyl-2,3,4,5-tetrahydro-1H-1,5-diazepin-1-yl]-N-isopropyl-N-(4-methoxyphenyl)acetamide (−12r, 0.500 g) in CH$_2$Cl$_2$ (10 mL) under argon was treated with methanesulfonyl chloride (0.266 mL) and diisopropylethylamine (0.598 mL). After several minutes, the reaction was transferred to a separatory funnel and washed with aqueous 1N NaHSO$_4$. The aqueous layer was back-extracted with CH$_2$Cl$_2$. The combined organic layers were dried over anhydrous MgSO$_4$, filtered and evaporated in vacuo. The residue was purified on flash grade silica gel eluting with 2:3 ethyl acetate/hexane. Fractions containing the product were combined, evaporated in vacuo and triturated with hexane. Hexane was removed in vacuo and the residual solid was dried under high vacuum to provide 2-[2,4-dioxo-3-(methanesulfonyloxymethylene)-5-phenyl-2,3,4,5-tetrahydro-1H-1,5-diazepin-1-yl]-N-isopropyl-N-(4-methoxyphenyl)acetamide (12s, 0.502 g) as a solid. The product was contaminated with approximately 40% of 2-[2,4-dioxo-3-methylene-5-phenyl-2,3,4,5-tetrahydro-1H-1,5-diazepin-1-yl]-N-isopropyl-N-(4-methoxyphenyl)acetamide which reacted equally well in the subsequent steps. $^1$H NMR (300 MHz, CDCl$_3$) 1.10 (d, J=7 Hz, 6H), 3.15 (s, 3H), 3.89 (s, 3H), 3.96 (d, J=2 Hz, 2H), 4.92 (m, 4H), 6.03 (m, 2H), 7.00 (m, 2H), 7.18 (m, 2H), 7.40 (m, 5H).
MS (ESI) [M+H]$^+$=516

2-[2,4-Dioxo-3-(2,3-dihydro-2-oxo-1H-benzimidazol-1-yl)methylene-5-phenyl-2,3,4,5-tetrahydro-1H-1,5-diazepin-1-yl]-N-isopropyl-N-(4-methoxyphenyl)acetamide (Example 12)

A solution of benzoximidazole (10.4 mg) in anhydrous DMF (1.5 mL) under argon was cooled to 0-5° C. Sodium bis(trimethylsilyl)amide (0.6 M in toluene, 129 μL) was added via micropipette followed by 2-[2,4-dioxo-3-(methanesulfonyloxymethylene)-5-phenyl-2,3,4,5-tetrahydro-1H-1,5-diazepin-1-yl]-N-isopropyl-N-(4-methoxyphenyl)acetamide [containing approximately 40% of 2-[2,4-dioxo-3-methylene-5-phenyl-2,3,4,5-tetrahydro-1H-1,5-diazepin-1-yl]-N-isopropyl-N-(4-methoxyphenyl)acetamide](12s, 20mg). The reaction was allowed to warm to ambient temperature and stir overnight. Addition sodium bis(trimethylsilyl)amide (0.6 M in toluene, 129 μL) was added via micropipette. After approximately 10 min., the reaction mixture was quenched with several drops of glacial acetic acid and evaporated in vacuo. The residue was partitioned between ethyl acetate and aqueous 1N NaHSO$_4$. The layers were separated and the aqueous layer was back-extracted with ethyl acetate. The combined organic layers were washed with brine, dried over anhydrous MgSO$_4$, filtered and evaporated in vacuo. The residue was purified on a preparative TLC plate (20×20 cm, 500 μM) eluting with 5% methanol in CH$_2$Cl$_2$. The product band was removed, eluted with 4:1 CH$_2$Cl$_2$/methanol, filtered and evaporated in vacuo. The residue was lyophilized from CH$_3$CN/H$_2$O to provide 2-[2,4-dioxo-3-(2,3-dihydro-2-oxo-1H-benzimidazol-1-yl)methylene-5-phenyl-2,3,4,5-tetrahydro-1H-1,5-diazepin-1-yl]-N-isopropyl-N-(4-methoxyphenyl)acetamide (10 mg) as a white lyophilate. $^1$H NMR (400 MHz, CDCl$_3$) 0.99 (m, 6H), 3.62 (d, J=16 Hz, 1H), 3.79 (s, 3H), 4.10 (d, J=16 Hz, 1H), 4.23 (t, J=6 Hz, 1H), 4.50 (m, 2H), 4.90 (m, 1H), 5.86 (d, J=6 Hz, 1H), 5.91 (d, J=6 Hz, 1H), 6.99 (m, 7H), 7.26 (m, 3H), 7.33 (m, 2H), 7.46 (d, J=8 Hz, 1H), 7.54 (s, 1H).

Preparation of Example 13

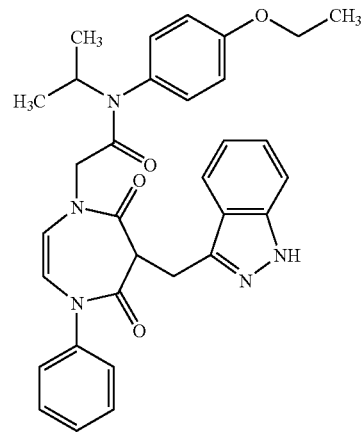

2-[2,4-Dioxo-3-(1H-indazol-3-ylmethylene)-5-phenyl-2,3,4,5-tetrahydro-1H-1,5-diazepin-1-yl]-N-(4-ethoxyphenyl)-N-isopropylacetamide (Example 13)

Synthesized via Reaction Scheme 2.
$^1$H NMR (400 MHz, DMSO-d$_6$) 7.79 (d, 1H), 7.50-7.13 (9H), 7.10 (t, 1H), 7.00 (d, 2H), 6.20 (m, 2H), 4.77 (sept, 1H) 4.15 (m, 1H), 4.10-3.95 (3H), 3.78 (d, 1H), 3.68 (m, 1H), 3.60-3.25 (2H), 1.34 (t, 3H), 0.97 (d, 6H). MS (ESI): M+H=552.

Preparation of Example 14

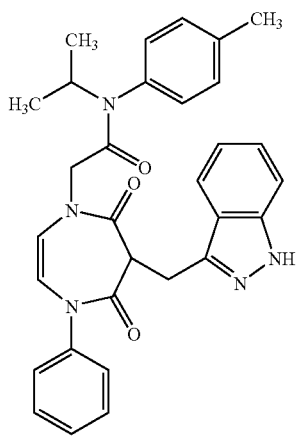

2-[2,4-Dioxo-3-(1H-indazol-3-ylmethylene)-5-phenyl-2,3,4,5-tetrahydro-1H-1,5-diazepin-1-yl]-N-isopropyl-N-(4-methylphenyl)acetamide (Example 14)

Synthesized via Reaction Scheme 1

$R_f$=0.1 (1:1 Hexanes/ethyl acetate). $^1$H NMR (300 MHz, CDCl$_3$) 7.85 (d, 1H), 7.50-7.00 (14H), 6.05 (m, 2H), 4.95 (sept, 1H) 4.25 (m, 1H), 3.95 (d, 1H), 3.85 (m, 1H), 3.70-3.60 (m, 1H), 2.39 (s, 3H), 1.05 (d, 6H). MS (ESI): M+H=522.

Preparation of Example 15

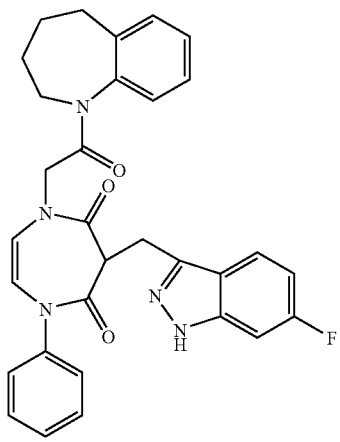

3-(6-Fluoro-1H-indazol-3-ylmethylene)-1-[2-oxoethyl-2-(2,3,4,5-tetrahydro-1H-1-benzazepin-1-yl)]-5-phenyl-1H-1,5-diazepine-2,4-dione (Example 15)

Synthesized via Reaction Scheme 1.

$^1$H NMR (300 MHz, DMSO-d$_6$) 7.83-7.91 (m, 1H); 7.22-7.50 (m, 10H); 6.95-7.01 (m, 1H); 6.28 (d, J=6.8 Hz, 1H); 6.22 (d, J=6.8, 1H); 4.13-4.50 (m, 3H); 3.71-3.95 (m, 1H); 3.36-3.59 (m, 2H); 2.55-2.93 (, 3H); 1.89-2.01 (m, 1H); 1.67-1.78 (m, 2H); 1.24-1.39 (m, 1H)

MS (ESI): M+H=538

Preparation of Example 16

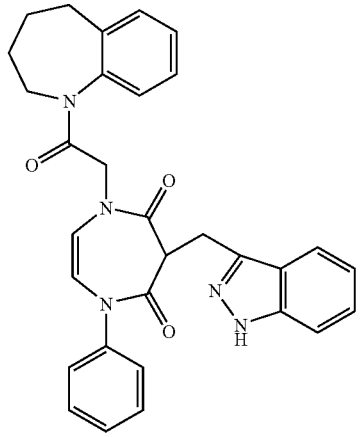

3-(1H-Indazol-3-ylmethylene)-1-[2-oxoethyl-2-(2,3,4,5-tetrahydro-1H-1-benzazepin-1-yl)]-5-phenyl-1H-1,5-diazepine-2,4-dione (Example 16)

Synthesized via Reaction Scheme 1.

$^1$H NMR (400 MHz, CDCl$_3$) 7.72-7.79 (m, 1H); 7.17-7.36 (m, 11H); 7.04-7.11 (m, 1H); 5.90-6.11 (m, 2H); 4.61-4.72 (m 1H); 3.66-4.31 (m, 4H); 3.47-3.65 (m, 1H); 2.85-3.02 (m, 1H); 2.60-2.73 (m, 2H); 1.72-2.01 (m. 3H); 1.28-1.43 (m, 1H)

MS (ESI): M+H=520

Preparation of Example 17

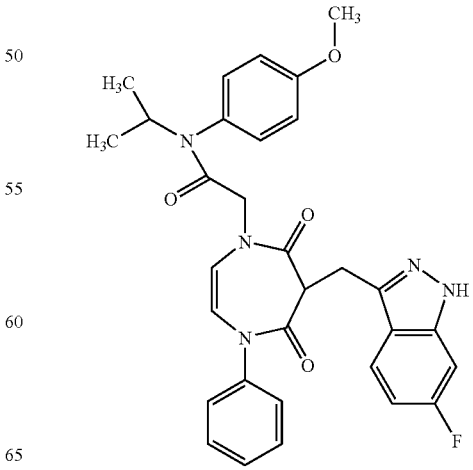

2-[2,4-Dioxo-3-(6-fluoro-1H-indazol-3-ylmethylene)-5-phenyl-2,3,4,5-tetrahydro-1H-1,5-diazepin-1-yl]-N-isopropyl-N-(4-methoxyphenyl)acetamide (Example 17)

Synthesized via Reaction Scheme 1.

$^1$H NMR (400 MHz, CDCl$_3$) 7.58-7.64 (m, 1H); 7.18-7.34 (m, 5H); 7.13-7.18 (m, 1H); 7.04-7.08 (m, 1H); 6.02 (d, J=6.2 Hz, 1H); 5.84-5.89 (m, 1H); 4.97 (q, J=6.8 Hz, 1H); 4.23 (dd, J=8.6 Hz, J=5.0 Hz, 1H); 4.05-4.09 (m, 1H); 3.80 (s, 3H); 3.70-3.82 (m, 2H); 3.36-3.44 (m, 1H); 1.05 (d, J=6.6 Hz, 6H). MS (ESI): M+H=556

Preparation of Example 18 (Enantiomer II)

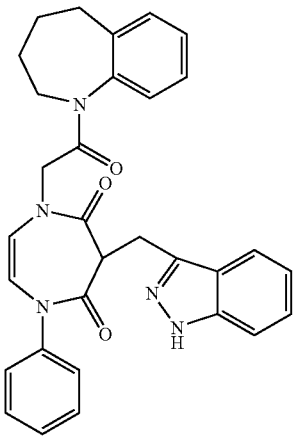

Chiral 3-(1H-Indazol-3-ylmethylene)-1-[2-oxoethyl-2-(2,3,4,5-tetrahydro-1H-1-benzazepin-1-yl)]-5-phenyl-1H-1,5-diazepine-2,4-dione (Example 18, Enantiomer #2 of Example 16)

Synthesised via Reaction Scheme 1.

Enantiomer #2 of Example 16 from chiral separation on Column Chiralcel OD (2×25 cm) from Chiral Technologies, 16 ml/min of MeOH (10% CHCl$_3$)), 45 g/min of CO2, 210 Bar, 40 C, 290 nm, 12.5 mg/inj $^1$H NMR (400 MHz, CDCl$_3$) 7.72-7.79 (m, 1H); 7.17-7.36 (m, 11H); 7.04-7.11 (m, 1H); 5.90-6.11 (m, 2H); 4.61-4.72 (m 1H); 3.66-4.31 (m, 4H); 3.47-3.65 (m, 1H); 2.85-3.02 (m, 1H); 2.60-2.73 (m, 2H); 1.72-2.01 (m. 3H); 1.28-1.43 (m, 1H) MS (ESI): M+H=520

Preparation of Example 19

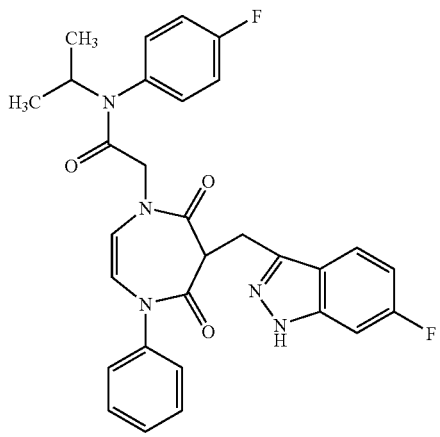

2-[2,4-Dioxo-3-(6-fluoro-1H-indazol-3-ylmethylene)-5-phenyl-2,3,4,5-tetrahydro-1H-1,5-diazepin-1-yl]-N-(4-fluorophenyl)-N-isopropylacetamide (Example 19)

Synthesized via Reaction Scheme 1.

$^1$H NMR (400 MHz, DMSO-d$_6$) 12.65 (s, 1H); 7.77-7.82 (m, 1H); 7.16-7.4 (m, 9H); 6.86-6.96 (m, 1H); 6.16 (bs, 1H); 4.75 (m, 1H); 3.96-4.13 (m, 1H); 3.75 (d, J=16.2 Hz, 1H); 3.24-3.50 (m, 1H); 3.29 (s, 3H); 0.94 (m, 6H). MS (ESI): M+H=544

Preparation of Example 20

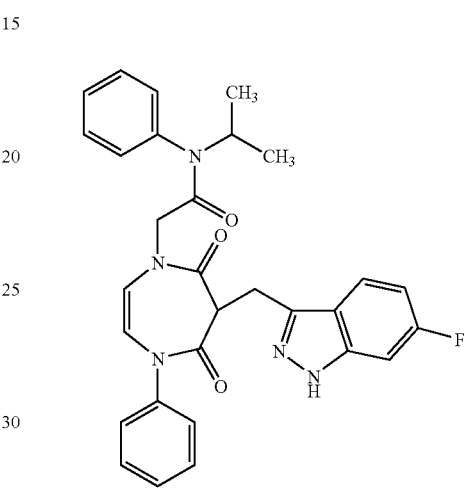

2-[2,4-Dioxo-3-(6-fluoro-1H-indazol-3-ylmethylene)-5-phenyl-2,3,4,5-tetrahydro-1H-1,5-diazepin-1-yl]-N-isopropyl-N-phenylacetamide (Example 20)

Synthesized via Reaction Scheme 1.

$^1$H NMR (300 MHz, CDCl$_3$): 7.71 (dd, J=8.8 Hz, J=5.3 Hz, 1H); 7.18-7.50 (m, 10H); 6.98 (dd, J=9.3 Hz, J=1.9 Hz, 1H); 6.87 (td, J=9.1 Hz, J=2.0 Hz, 1H); 6.05 (d, J=6.6 Hz, 1H); 5.95 (d, J=6.6 Hz, 1H); 5.01 (q, J=6.7 Hz, 1H); 3.74-4.28 (m, 5H); 3.46-3.56 (m, 1H); 1.09 (m, 6H). (MS (FAB) [M+H]$^+$=526.

Preparation of Example 21 (Enantiomer II of Example 20)

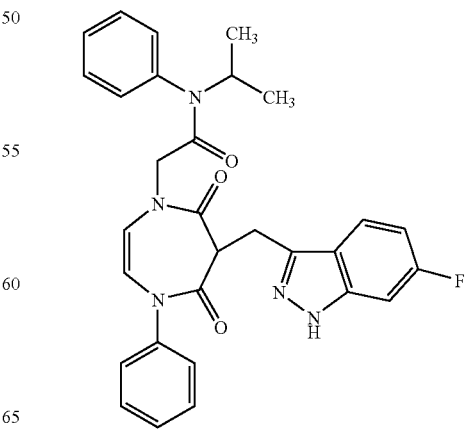

(Chiral) 2-[2,4-Dioxo-3-(6-fluoro-1H-indazol-3-ylmethylene)-5-phenyl-2,3,4,5-tetrahydro-1H-1,5-diazepin-1-yl]-N-isopropyl-N-phenylacetamide (Example 21, Enantiomer #2 of Example 20)

Synthesized via Reaction Scheme 1.
Enantiomer #2 of Example 20 from chiral separation on column Chiralcel OJ (2×25 cm) from Chiral Technologies, 7.9 ml/min of EtOH, 45 g/min of $CO_2$, 210 Bar, 40 C, 220 nm, 23 mg/inj
$^1$H NMR (300 MHz, $CDCl_3$): 7.71 (dd, J=8.8 Hz, J=5.3 Hz, 1H); 7.18-7.50 (m, 10H); 6.98 (dd, J=9.3 Hz, J=1.9 Hz, 1H); 6.87 (td, J=9.1 Hz, J=2.0 Hz, 1H); 6.05 (d, J=6.6 Hz, 1H); 5.95 (d, J=6.6 Hz, 1H); 5.01 (q, J=6.7 Hz, 1H); 3.74-4.28 (m, 5H); 3.46-3.56 (m, 1H); 1.09 (m, 6H). MS (FAB) [M+H]$^+$=526.

Preparation of Example 22

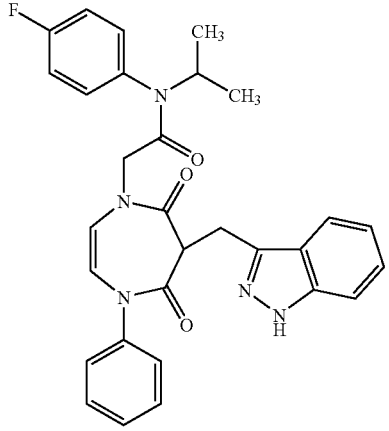

2-[2,4-Dioxo-3-(1H-indazol-3-ylmethylene)-5-phenyl-2,3,4,5-tetrahydro-1H-1,5-diazepin-1-yl]-N-(4-fluorophenyl)-N-isopropylacetamide (Example 22)

Synthesized via Reaction Scheme 1.
$^1$H NMR (400 MHz, DMSO-$d_6$): 12.58 (s, 1H); 7.75 (d, J=8.0 Hz, 1H); 7.22-7.44 (m, 11H); 7.05 (t, J=7.5 Hz, 1H); 6.16 (bs, 1H); 4.75 (q, J=6.6 Hz, 1H); 4.14 (t, J=7.0 Hz, 1H); 3.98 (d, J=6.3 Hz, 1H); 3.75 (d, J=6.3 Hz, 1H); 3.30-3.54 (m, 3H); 0.94 (d, J=6.8 Hz, 6H).
MS (FAB) [M+H]$^+$=526.

Preparation of Example 23

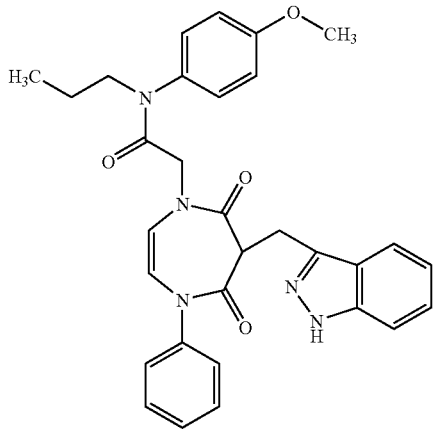

2-[2,4-Dioxo-3-(1H-indazol-3-ylmethylene)-5-phenyl-2,3,4,5-tetrahydro-1H-1,5-diazepin-1-yl]-N-(4-methoxyphenyl)-N-propylacetamide (Example 23)

Synthesized via Reaction Scheme 2.
$^1$H NMR (400 MHz, DMSO-$d_6$) 7.74 (d, 1H), 7.39 (t, 3H), 7.30-7.15 (m, 6H), 7.03 (t, 1H), 6.97 (d, 2H), 6.14 (dd, 2H), 5.25 (br.s, 1H), 4.11 (dd, 2H), 3.86 (d, 1H), 3.72 (s, 3H), 3.60-3.25 (m, 4H), 1.34 (m, 2H), 0.76 (t, 3H). MS (ESI): M+H=538.

Preparation of Example 24 (Enantiomer I of Example 16)

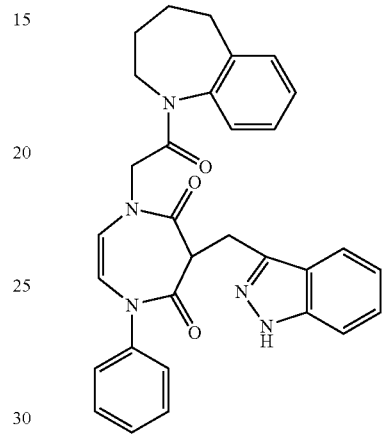

(Chiral) 3-(1H-Indazol-3-ylmethylene)-1-[2-oxoethyl-2-(2,3,4,5-tetrahydro-1H-1-benzazepin-1-yl)]-5-phenyl-1H-1,5-diazepine-2,4-dione (Example 24, Enantiomer #1 of Example 16)

Synthesized via Reaction Scheme 1
Enantiomer #1 of Example 16 from chiral separation on Column Chiralcel OD (2×25 cm) from Chiral Technologies, 16 ml/min of MeOH (10% $CHCl_3$)), 45 g/min of $CO_2$, 210 Bar, 40 C, 290 nm, 12.5 mg/inj
$^1$H NMR (400 MHz, $CDCl_3$) 7.72-7.79 (m, 1H); 7.17-7.36 (m, 11H); 7.04-7.11 (m, 1H); 5.90-6.11 (m, 2H); 4.61-4.72 (m 1H); 3.66-4.31 (m, 4H); 3.47-3.65 (m, 1H); 2.85-3.02 (m, 1H); 2.60-2.73 (m, 2H); 1.72-2.01 (m. 3H); 1.28-1.43 (m, 1H) MS (ESI): M+H=520

Preparation of Example 25

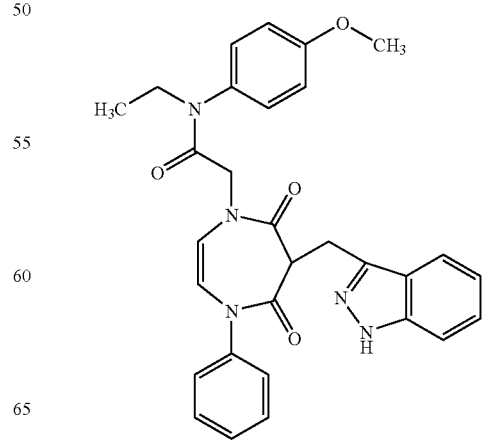

2-[2,4-Dioxo-3-(1H-indazol-3-ylmethylene)-5-phenyl-2,3,4,5-tetrahydro-1H-1,5-diazepin-1-yl]-N-ethyl-N-(4-methoxyphenyl)acetamide (Example 25)

Synthesized via Reaction Scheme 2.

$^1$H NMR (400 MHz, DMSO-d$_6$) 12.61 (s, 1H), 7.78 (d, 1H), 7.43 (m, 3H), 7.40-7.25 (m, 6H), 7.08 (t, 1H), 7.03 (d, 2H), 6.19 (q, 2H), 4.16 (t, 1H), 4.01 (dd, 2H), 3.77 (s, 3H), 3.60 (q, 2H), 3.46 (dq, 2H), 0.98 (t, 3H). MS (ESI): M+H=524.

Preparation of Example 26

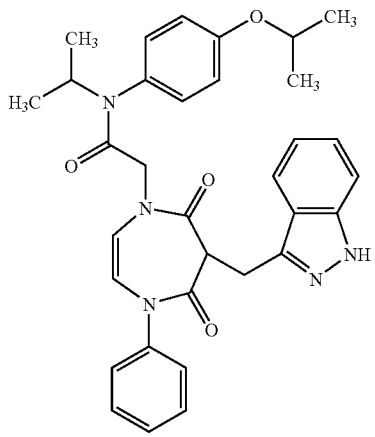

2-[2,4-Dioxo-3-(1H-indazol-3-ylmethylene)-5-phenyl-2,3,4,5-tetrahydro-1H-1,5-diazepin-1-yl]-N-(4-isopropoxyphenyl)-N-isopropylacetamide (Example 26)

Synthesized via Reaction Scheme 2

$^1$H NMR (400 MHz, DMSO-d$_6$) 12.59 (s, 1H), 7.78 (d, 1H), 7.43 (t, 3H), 7.40-7.25 (m, 4H), 7.15 (br. s, 2H), 7.08 (t, 1H) 7.00 (d, 2H), 6.18 (q, 2H), 4.75 (sept, 1H), 4.63 (sept, 1H), 4.15 (t, 1H), 3.90 (dd, 2H), 3.47 (dq, 2H), 1.27 (d, 6H), 0.96 (d, 6H). MS (ESI): M+H=566.

Preparation of Example 27

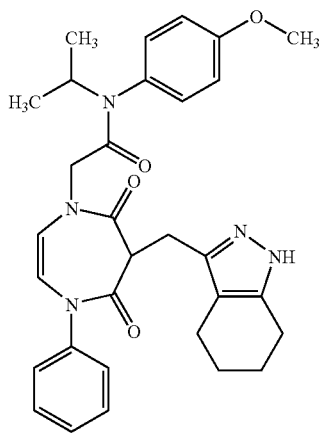

2-[2,4-Dioxo-5-phenyl-3-(4,5,6,7-tetrahydro-1H-indazol-3-ylmethylene)-2,3,4,5-tetrahydro-1H-1,5-diazepin-1-yl]-N-isopropyl-N-(4-methoxyphenyl)acetamide (Example 27)

via Reaction Scheme 3

Intermediate 27t 3-carbomethoxy-1-[2-(trimethylsilyl)-1-ethyloxymethylene]-H-indazole A solution of 3-carbomethoxyindazole (2.500 g) in anhydrous THF (25 mL) was cooled under argon to 0-5° C. and treated with potassium bis(trimethylsilyl)amide (0.5 M in toluene, 34.1 mL) added dropwise via an addition funnel followed by chloromethyl 2-(trimethylsilyloxy)-1-ethyl ether (3.01 mL) approximately 5 minutes later. After approximately 10 min., the reaction was quenched with glacial acetic acid and evaporated in vacuo. The residue was partitioned between ethyl acetate and aqueous 1N NaHSO$_4$. The layers were separated and the aqueous layer was back-extracted with ethyl acetate. The combined organic layers were dried over anhydrous MgSO$_4$, filtered and evaporated in vacuo. The crude product was purified on flash grade silica gel eluting with 1:9 ethyl acetate/hexane. Fractions containing the product were combined, evaporated in vacuo and dried under high vacuum to provide 3-carbomethoxy-1-[2-(trimethylsilyl)-1-ethyloxymethylene]-1H-indazole (27t, 2.687 g) as an oil. $^1$H NMR (300 MHz, CDCl$_3$)-0.09 (s, 9H), 0.86 (t, J=8 Hz, 2H), 3.55 (t, J=8 Hz, 2H), 4.04 (s, 3H), 5.82 (s, 2H), 7.35 (t, J=8 Hz, 1H), 7.47 (t, J=8 Hz, 1H), 7.65 (d, J=8 Hz, 1H), 8.23 (d, J=8 Hz, 1H). MS (ESI) [M+Na]$^+$=329

Intermediate 27u 3-carbomethoxy-1-[2-(trimethylsilyl)-1-ethyloxymethylene]-4,5,6,7-tetrahydro-1H-indazole A mixture of 3-carbomethoxy-1-[2-(trimethylsilyl)-1-ethyloxymethylene]-1H-indazole (27t, 2.455 g) and platinum oxide (0.50 g) in glacial acetic acid (15 mL) was hydrogenated at 50 psi for approximately 20 hrs. After filtration, the reaction mixture was evaporated in vacuo and the residue was partitioned between CH$_2$Cl$_2$ and aqueous K$_2$CO$_3$ (5% w/v). After separating the layers, the organic phase was back-extracted with CH$_2$Cl$_2$. The combined organic layers were dried over anhydrous MgSO$_4$, filtered, evaporated in vacuo and dried under high vacuum to provide 3-carbomethoxy-1-[2-(trimethylsilyl)-1-ethyloxymethylene]-4,5,6,7-tetrahydro-1H-indazole (27u, 2.456 g) as a solid.). $^1$H NMR (400 MHz, CDCl$_3$)-0.05 (s, 9H), 0.87 (t, J=8 Hz, 2H), 1.78 (m, 4H), 2.67 (t, J=6 Hz, 2H), 2.74 (t, J=6 Hz, 2H), 3.85 (t, J=9 Hz, 2H), 3.90 (s, 3H), 5.41 (s, 2H).

MS (ESI) [M+H]$^+$=311

Intermediate 27v 3-hydroxymethylene-1-[2-(trimethylsilyl)-1-ethyloxymethylene]-4,5,6,7-tetrahydro-1H-indazole A solution of 3-carbomethoxy-1-[2-(trimethylsilyl)-1-ethyloxymethylene]-4,5,6,7-tetrahydro-1H-indazole (27u, 2.198 g) in anhydrous THF (10 mL) was cooled to 0-5° C. and treated dropwise over approximately 5 minutes with a solution of lithium aluminum hydride (1.0 M in THF, 7.4 mL). After stirring an additional 15 min., the reaction was poured carefully into a solution of aqueous 1N NaHSO$_4$ with stirring and then diluted with ethyl acetate. The mixture was transferred to a separatory funnel and the layers were separated. The aqueous layer was back-extracted twice with ethyl acetate and the combined organic layers were washed with brine, dried over anhydrous $MgSO_4$, filtered and evaporated in vacuo. Drying under high vacuum provided 3-hydroxymethylene-1-[2-(trimethylsilyl)-1-ethyloxymethylene]-4,5,6,7-tetrahydro-1H-indazole (27v, 1.972 g) as an oil. $^1$H NMR (300 MHz, $CDCl_3$)-0.04 (s, 9H), 0.88 (t, J=8 Hz, 2H), 1.77 (m, 4H), 2.07 (b, 1H), 2.48 (t, J=6 Hz, 2H), 2.62 (t, J=6 Hz, 2H), 3.54 (t, J=8 Hz, 2H), 4.60 (s, 2H), 5.28 (s, 2H).

MS (ESI) $[M+H]^+$=283

Intermediate 27w 3-methanesulfonoxymethylene-1-[2-(trimethylsilyl)-1-ethyloxymethylene]-4,5,6,7-tetrahydro-1H-indazole A solution of 3-hydroxymethylene-1-[2-(trimethylsilyl)-1-ethyloxymethylene]-4,5,6,7-tetrahydro-1H-indazole (27u, 1.732 g) and diisopropylethylamine (4.28 mL) in dichloromethane (5 mL) was cooled under argon to 0-5° C. Methanesulfonic anhydride (2.140 g) was added and the mixture was stirred for approximately 10 minutes. The reaction was diluted with $CH_2Cl_2$, transferred to a separatory funnel and washed with aqueous 1N $NaHSO_4$. After separating the layers, the aqueous phase was back-extracted with $CH_2Cl_2$. The combined organic layers were washed with aqueous $K_2CO_3$ (5% w/v), dried over anhydrous $MgSO_4$, filtered and evaporated in vacuo. The crude material was purified on flash grade silica gel eluting with 7:3 hexane/ethyl acetate. Fractions containing the product were combined, evaporated in vacuo and dried under high vacuum to provide 3-methanesulfonoxymethylene-1-[2-(trimethylsilyl)-1-ethyloxymethylene]-4,5,6,7-tetrahydro-1H-indazole (27w, 0.938 g) as an oil. $^1$H NMR (400 MHz, $CDCl_3$)-0.04 (s, 9H), 0.87 (m, 2H), 1.78 (m, 4H), 2.53 (t, J=6 Hz, 2H), 2.64 (t, J=6 Hz, 2H), 2.96 (s, 3H), 3.53 (t, J=8 Hz, 2H), 5.20 (s, 2H), 5.30 (s, 2H).

2-[2,4-dioxo-5-phenyl-3-(4,5,6,7-tetrahydro-1H-indazol-3-ylmethylene)-2,3,4,5-tetrahydro-1H-1,5-diazepin-1-yl]-N-isopropyl-N-(4-methoxyphenyl) acetamide (Example 27)

A solution of 2-(2,4-dioxo-5-phenyl-2,3,4,5-tetrahydro-1H-1,5-diazepin-1-yl)-N-isopropyl-N-(4-methoxyphenyl) acetamide (12p, 100 mg) in anhydrous DMF (2 mL) under an atmosphere of argon was treated with sodium bis(trimethylsilyl)amide (0.6 M in toluene, 0.430 mL). After stirring several minutes, a solution of 3-methanesulfonoxymethylene-1-[2-(trimethylsilyl)-1-ethyloxymethylene]-4,5,6,7-tetrahydro-1H-indazole(27w, 97 mg) in anhydrous DMF (1 mL) was added. After 15 min., the reaction mixture was treated with additional sodium bis(trimethylsilyl)amide (0.6 M in toluene, 0.246 mL). After stirring for an additional 45 min., the reaction mixture was quenched with several drops of glacial acetic acid and then evaporated in vacuo. The residue was partitioned between ethyl acetate and aqueous 1N $NaHSO_4$ and then transferred to a separatory funnel. The layers were separated and the aqueous phase was back-extracted with ethyl acetate. The combined organic layers were washed with brine, dried over anhydrous $MgSO_4$, filtered, and evaporated in vacuo. The residue was combined with trifluoroacetic acid (TFA) (~3 mL) and stirred under Argon for approximately 30 min. The mixture was concentrated in vacuo and the residue was partitioned between $CH_2Cl_2$ and aqueous $K_2CO_3$ (5% w/v). After separating the layers, the aqueous phase was back-extracted with $CH_2Cl_2$. The combined organic phases were dried over anhydrous $MgSO_4$, filtered and evaporated in vacuo. The crude product was purified on flash grade silica gel eluting with ethyl acetate followed by 5% methanol in $CH_2Cl_2$. Fractions containing the product were combined, evaporated in vacuo and purified again on a preparative TLC plate (20×20 cm, 500 ☐M) eluting with 5% methanol in $CH_2Cl_2$. The product band was removed, eluted with 20% methanol in $CH_2Cl_2$, filtered and evaporated in vacuo. The residue was lyophilized from $CH_3CN$ and $H_2O$ to provide 2-[2,4-dioxo-5-phenyl-3-(4,5,6,7-tetrahydro-1H-indazol-3-ylmethylene)-2,3,4,5-tetrahydro-1H-1,5-diazepin-1-yl]-N-isopropyl-N-(4-methoxyphenyl)acetamide (Example 27, 49 mg) as a white lyophilate. $^1$H NMR (400 MHz, $CDCl_3$) 1.02 (d, 2 Hz, 3H), 1.04 (d, 2 Hz, 3H), 1.72 (m, 4H), 2.41 (t, J=6 Hz, 2H), 2.60 (t, J=6 Hz, 2H), 3.27 (m, 2H), 3.61 (t, J=6 Hz, 1H), 3.81 (s, 3H), 3.86 (d, J=17 Hz, 1H), 3.95 (d, J=17 Hz, 1H), 4.95 (m, 1H), 5.88 (d, J=6 Hz, 1H), 5.94 (d, J=6 Hz, 1H), 6.92 (m, 2H), 7.10 (m, 2H), 7.25 (m, 4H), 7.35 (m, 2H).

MS (ESI) $[M+H]^+$=542

Preparation of Example 28 (Enantiomer I)

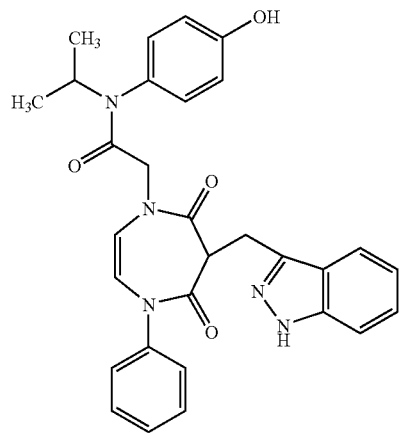

(Chiral) 2-[2,4-Dioxo-3-(1H-indazol-3-ylmethylene)-5-phenyl-2,3,4,5-tetrahydro-1H-1,5-diazepin-1-yl]-N-(4-hydroxyphenyl)-N-isopropylacetamide (Enantiomer #1 of Example 28)

To the solution of 2-[2,4-dioxo-3-(1H-indazol-3-ylmethylene)-5-phenyl-2,3,4,5-tetrahydro-1H-1,5-diazepin-1-yl]-N-isopropyl-N-(4-methoxyphenyl)acetamide (Example 1) (1 g, 1.86 mM) in 50 ml of dichloromethane was cooled to 0° C. and 10 fold excess of $BBr_3$ was added. The reaction mixture was stirred for 3 hrs at room temp., cooled to 0° C. and methanol was added dropwise. Organic solvents were evaporated under reduced pressure and residue was purified using column chromatography on silica gel using mixture of Hexane-Ethyl Acetate (1:3) as an eluent providing 700 mg of pure racemic product.

The racemate was separated on column Chiralpak AS (2×25 cm) from Chiral Technologies, 7.7 ml/min of EtOH, 45 g/min of CO2, 210 Bar, 40 C, 270 nm, 10 mg/inj yielding 250 mg of product eluting as the first enantiomer (Enantiomer #1).

$^1$H NMR (400 MHz, CDCl$_3$) 7.76 (d, J=7.8 Hz, 1H); 7.16-7.30 (m, 8H); 7.02-7.08 (m, 1H); 6.66-6.95 (m, 3H); 5.82-5.89 (m, 2H); 4.87 (q, J=6.8 Hz, 1H); 3.63-3.96 (m, 4H); 0.97 (two d, J=6.6 Hz, 6H). MS (FAB) [M+H]$^+$=524.

Preparation of Example 29

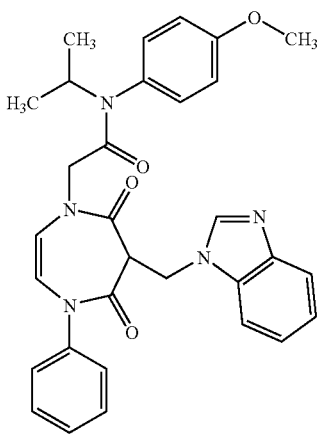

2-[2,4-Dioxo-3-(1H-benzimidazol-1-ylmethylene)-5-phenyl-2,3,4,5-tetrahydro-1H-1,5-diazepin-1-yl]-N-isopropyl-N-(4-methoxyphenyl)acetamide (Example 29)

via Reaction Scheme 3.

A solution of benzimidazole (9.2 mg) in anhydrous DMF (1.5 mL) under argon was cooled to 0-5° C. Sodium bis(trimethylsilyl)amide (0.6 M in toluene, 129 μL) was added via micropipette followed by (1-{2-[isopropyl(4-methoxyphenyl)amino]-2-oxoethyl}-5,7-dioxo-4-phenyl-4,5,6,7-tetrahydro-1H-1,4-diazepin-6-yl)methyl methanesulfonate (20 mg). After approximately 10 min., the reaction mixture was quenched with several drops of glacial acetic acid and evaporated in vacuo. The residue was partitioned between ethyl acetate and aqueous K$_2$CO$_3$ (5% w/v). The layers were separated and the aqueous layer was back-extracted with ethyl acetate. The combined organic layers were dried over anhydrous MgSO$_4$, filtered and evaporated in vacuo. The residue was purified on a preparative TLC plate (20×20 cm, 500 □M) eluting with 5% methanol in CH$_2$Cl$_2$. The product band was removed, eluted with 4:1 CH$_2$Cl$_2$/methanol, filtered and evaporated in vacuo. The residue was lyophilized from CH$_3$CN/H$_2$O to provide 2-[6-(1H-benzimidazol-1-ylmethyl)-5,7-dioxo-4-phenyl-4,5,6,7-tetrahydro-1H-1,4-diazepin-1-yl]-N-isopropyl-N-(4-methoxyphenyl)acetamide as a white lyophilate (15 mg). $^1$H NMR (300 MHz, CDCl$_3$) 1.13 (m, 6H), 3.86 (m, 1H), 3.90 (s, 3H), 3.97 (d, J=4 Hz, 2H), 4.90 (m, 1H), 5.07 (m, 2H), 5.90 (d, J=7 Hz, 1H), 5.99 (d, J=7 Hz, 1H), 7.01 (m, 2H), 7.18 (m, 2H), 7.33 (m, 8H), 7.85 (m, 1H), 8.26 (s, 1H).

MS (ESI) [M+H]$^+$=538

Preparation of Example 30

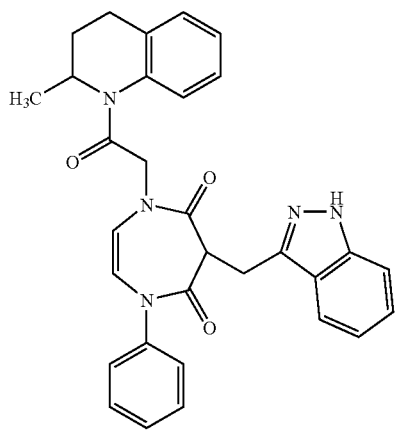

1-[2-(3,4-Dihydro-2H-2-methylquinolin-1-yl)-2-oxoethyl]-3-(1H-indazol-3-ylmethylene)-5-Phenyl-1H-1,5-diazepine-2,4-dione (Example 30)

Synthesized via Reaction Scheme 2.

$^1$H NMR (300 MHz, DMSO-d$_6$) 12.60 (s, 1H), 7.82 (m, 1H), 7.56-7.18 (10H), 7.11 (q, 1H), 6.39-6.16 (m, 2H), 4.81 (dd, 2H), 4.66 (m, 1H), 4.38-4.90 (2H), 3.52 (dq, 2H), 2.65 (m, 1H), 2.46 (m, 1H), 2.33 (m, 1H), 1.29 (m, 1H), 1.07 (d, 3H). MS (ESI): [M+H]=520.

Preparation of Example 31

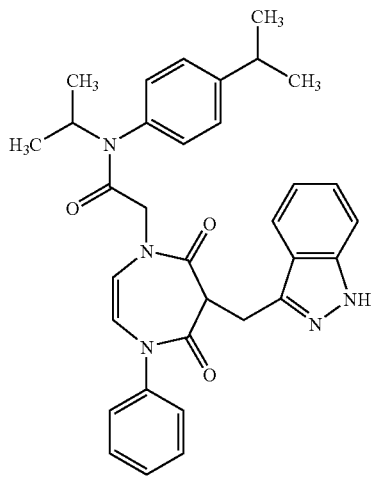

2-[2,4-Dioxo-3-(1H-indazol-3-ylmethylene)-5-phenyl-2,3,4,5-tetrahydro-1H-1,5-diazepin-1-yl]-N-isopropyl-N-(4-isopropylphenyl)acetamide (Example 31)

Synthesized via Reaction Scheme 2.

$^1$H NMR (400 MHz, DMSO-d$_6$) 12.60 (s, 1H), 7.79 (d, 1H), 7.43 (2H), 7.41-7.25 (6H), 7.20 (br. s, 2H), 7.09 (t, 1H) 6.19 (q, 2H) 4.78 (sept, 1H), 4.16 (t, 1H), 3.89 (dd, 2H), 4.00-3.64 (1H), 3.48 (dq, 2H), 2.95 (sept, 1H), 1.23 (d, 6H), 0.98 (d, 6H). MS (ESI): [M+H]=550.

Preparation of Example 32 (Enantiomer II)

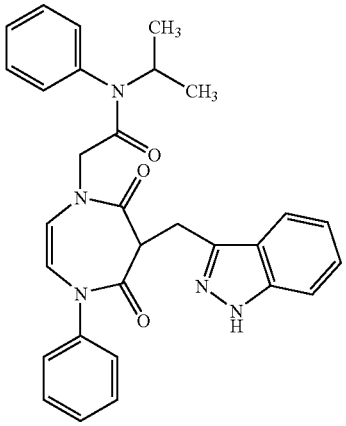

(Chiral) 2-[2,4-Dioxo-3-(1H-indazol-3-ylmethylene)-5-phenyl-2,3,4,5-tetrahydro-1H-1,5-diazepin-1-yl]-N-isopropyl-N-phenylacetamide (Enantiomer #2 of Example 32)

Synthesized via Reaction Scheme 1.

Enantiomer #2 from chiral separation of racemic 2-[2,4-dioxo-3-(1H-indazol-3-ylmethylene)-5-phenyl-2,3,4,5-tetrahydro-1H-1,5-diazepin-1-yl]-N-isopropyl-N-phenylacetamide on column Chiralcel OJ (2×25 cm) from Chiral Technologies, 9.9 ml/min of EtOH, 45 g/min of CO2, 210 Bar, 40 C, 220 nm, 25 mg/inj $^1$H NMR (400 MHz, CDCl$_3$): 7.82 (d, J=9 Hz, 1H); 7.09-7.47 (m, 13H); 6.03 (d, J=6.2, 1H); 5.98 (d, J=6.2 Hz, 1H); 4.98 (q, J=6.8 Hz, 1H); 4.26 (dd, J=7.8 Hz, J=2.0 Hz, 1H); 3.97 (d, J=16.5 Hz, 1H); 3.88 (d, J=16.5, 1H); 3.78-3.86 (m, 1H); 3.63 (dd, J=16.3 Hz, J=5.5 Hz, 1H); 1.05-1.92 (m, 6H). MS (FAB) [M+H]$^+$=508.

Example 33

2-[2,4-Dioxo-3-(1H-indazol-3-ylmethylene)-5-phenyl-2,3,4,5-tetrahydro-1H-1,5-diazepin-1-yl]-N-isopropyl-N-(4-methoxyphenyl)acetamide (Example 33—the same compound as in Example 1)

via Solid Phase Synthesis (Reaction Scheme 4)

Intermediate 1aa 1-benzyloxycarbonyl-3,4-dihydroxycyclohexane

Benzyl 7-oxabicyclo[4.1.0]heptane-3-carboxylate (2.60 g) obtained from commercially available starting materials by standard methods in dioxane (40 ml) and water (10 ml) was treated with 70% perchloric acid (3.25 g) diluted to 10 ml with water. The solution was stirred at ambient temperature overnight then diluted with water and treated with aq. NaHCO$_3$ until pH~10. The mixture was extracted with ethyl acetate (3×50 ml). The combined extracts were dried with anhydrous Na$_2$SO$_4$ and concentrated in vacuo to give the title compound (1aa, 2.76 g). $^1$H NMR (CDCl$_3$+TMS) 7.35 (m, 5H), 5.13 (m, 2H), 3.61 (m, 1H), 3.42 (m, 1H), 2.8 (m, 1H), 1.4-2.4 (m, 8H). MS ES+ m/z 273 [M+Na]$^+$.

Intermediate 1bb benzyl 2-(bromomethyl)hexahydro-1,3-benzodioxole-5-carboxylate 1-benzyloxycarbonyl-3,4-dihydroxycyclohexane 2-bromoacetaldehyde acetal 1-Benzyloxycarbonyl-3,4-dihydroxycyclohexane (1aa) in toluene (10 ml) and benzene (10 ml) was treated with 2-bromo-1,1-dimethoxyethane (1.72 g) and p-toluenenesulfonic acid monohydrate (41 mg). The solution was heated to reflux for 1 hr, and a few drops of benzene were removed by distillation. The solution was diluted with ethyl acetate (20 ml) and washed with aq. NaHCO$_3$ (3×20 ml). The organic phase was dried with anhydrous Na$_2$SO$_4$ and concentrated in vacuo to give 0.8 g of the title compound (1 bb). $^1$H NMR (CDCl$_3$+TMS) 7.35 (m, 5H), 5.33 (m, 1H), 5.15 (m, 2H), 3.35 (m, 4H), 2.91 (m, 1H), 2.71 (m, 1H), 2.50 (m, 1H), 2.35 (m, 1H), 2.1 (m, 1H), 1.4-1.8 (m, 2H). MS CI+m/z 372, 374 [M+NH$_4$]$^+$.

Intermediate 1ee

Tentagel-aminocarbonyl-3,4-dihydroxycyclohexane 2-bromoacetaldehyde acetal

1-Benzyloxycarbonyl-3,4-dihydroxycyclohexane 2-bromoacetaldehyde acetal (1 bb, 0.8 g) in 75% THF/water (20 ml) at 0° C. was treated with LiOH monohydrate (95 mg) and stirred at 0° C. for 1.5 Hr. The reaction was treated with 1M NaHSO$_4$ until pH~3 then diluted with water and separated. The aqueous phase was further extracted with ethyl acetate (3×20 ml). The THF and ethyl acetate extracts were combined, dried with Na$_2$SO$_4$, and concentrated in vacuo. The carboxylic acid intermediate (1cc), thus obtained, was taken up in dry DMF (5 ml) at 0° C. and treated with coupling agent HOBt (282 mg), followed by coupling agent EDC-methiodide (613 mg), both added portionwise over 5 min. The resulting solution was transferred to a suspension of pre-swollen amino functionalized Tentagel resin (SPS-Nu, 1dd, ≦0.25 mmole —NH$_2$/g; 1.65 g) in DMF. The mixture was sealed and mixed overnight. The resin was drained and washed with DMF (3×5 ml) and CH$_2$Cl$_2$ (4×5 ml) then dried under dry nitrogen stream to provide the title solid supported sample of Tentagel-aminocarbonyl-3,4-dihydroxycyclohexane 2-bromoacetaldehyde acetal (1ee). $^1$H NMR (300 MHz, CDCl$_3$) pre-saturation of styrene —CH=CH—: 5.3 (s, Br—CH$_2$—CH), 3.8 (bs, CH), 3.4 (bs, CH$_2$).

2-[2,4-dioxo-3-(1H-indazol-3-ylmethylene)-5-phenyl-2,3,4,5-tetrahydro-1H-1,5-diazepin-1-yl]-N-isopropyl-N-(4-methoxyphenyl)acetamide (Example 33—the same compound as in Example 1)

The Tentagel-aminocarbonyl-3,4-dihydroxycyclohexane 2-bromoacetaldehyde acetal (1ee, ≦0.1 mmole substitution), suspended in dry DMSO (5 ml), was treated with K$_2$CO$_3$ (141 mg) and aniline (0.47 g). The mixture was stirred under nitrogen and heated at 60° C. for 24 Hrs. The resin was drained and washed with DMSO (2×5 ml), 50% H$_2$O/DMSO (3×5 ml), H$_2$O (3×5 ml), DMSO (3×5 ml), and CH$_2$Cl$_2$ (4×5 ml), then dried in vacuo.

The solid supported aniline-derived sample (1ff, ≦0.10 mmole) suspended in dry CH$_2$Cl$_2$ (4 ml) was treated with triethylamine (61 mg) followed by methyl malonyl chloride (55 mg) The mixture was sealed under nitrogen and agitated overnight. The resin was drained, washed with $CH_2Cl_2$ (5×5 ml) and dried in vacuo. The entire procedure was repeated once.

The solid supported methyl malonyl amide sample (1gg, ≦0.10 mmole) preswollen in THF was treated with a solution of LiOH monohydrate (23 mg) in 75% THF/$H_2O$ (4 ml). The mixture was agitated for 3 hrs then drained and washed with 50% THF/$H_2O$ (4×5 ml), THF (4×5 ml), MeOH (4×5 ml), and $CH_2Cl_2$ (4×5 ml) then dried in vacuo to yield the solid supported malonic mono-amide mono-carboxylic acid (1hh).

The solid supported sample (1hh, ≦0.10 mmole), suspended in dry DMF (5 ml), was treated with the coupling agent HOBt (68 mg) followed by the coupling agent EDC methiodide salt (151 mg). $N^1$-isopropyl-$N^1$-(4-methoxyphenyl)glycinamide (1f, 116 mg) was added and the mixture was sealed under nitrogen and agitated overnight to yield the solid supported malonic diamide(1ii). The resin was drained and washed with DMF (4×5 ml) and $CH_2Cl_2$ (4×5 ml) then dried in vacuo.

The solid supported sample (1ii, ≦0.10 mmole) suspended in DMSO (5 ml) was treated with DBU (76 mg). The mixture was agitated for 30 min. then treated with tert-butyl 3-(bromomethylene)-1H-indazole-1-carboxylate (1 h, 155 mg). The mixture was agitated for 2 hrs, drained, and washed with DMSO (4×5 ml). The procedure was repeated twice, then the resin was drained and washed with DMSO (4×5 ml), MeOH (4×5 ml), and $CH_2Cl_2$ (4×5 ml) and dried under vacuum to yield the solid supported 2-alkylated malonic diamide(1jj).

The solid supported sample (1jj), suspended in dry toluene (5 ml), was treated with 0.4M anhydrous p-toluenesulfonic acid in toluene (0.5 ml). The mixture was heated at 60° C. for 2.5 Hrs. The mixture was filtered and the resin was washed with $CH_2Cl_2$ (3×5 ml) and EtOAc (3×5 ml). The combined filtrates were concentrated in vacuo then diluted with EtOAc, washed with saturated aq. $NaHCO_3$ (3×5 ml), dried with $Na_2SO_4$, and concentrated in vacuo to give the title compound (Example 33), plus the Boc-protected derivative of Example 33, namely, 2-[2,4-dioxo-3-(1-tert-butyloxycarbonyl-1H-indazol-3-ylmethylene)-5-phenyl-2,3,4,5-tetrahydro-1H-1,5-diazepin-1-yl]-N-isopropyl-N-(4-methoxyphenyl)acetamide. Treatment of this mixture with trifluoroacetic acid (TFA) afforded the pure titled compound (Example 33). MS ES– m/z 536 [M–H]$^-$, HPLC [$R^P$—C8, 10-100% $CH_3CN$/H2O (0.1% TFA)/20 min. UV det.] ret. time=Example 1 produced by Method A.

Abbreviations used:

| | |
|---|---|
| THF | Tetrahydrofuran |
| HOBT | N-Hydroxybenzotriazole |
| DMF | Dimethylformamide |
| EDC | 1-(-3-Dimethylaminopropyl)-3-ethylcardodiimide Hydrochloride |
| TFA | Trifluoroacetic acid |
| DMSO | Dimethylsulfoxide |
| DMSO-$d_6$ | Deuterodimethylsulfoxide |
| NaHMDS | Sodium Bis(trimethylsilyl)amide |
| LiOH | Lithium Hydroxide |
| DBU | 1,8-Diazabicyclo[5.4.0]undec-7-ene |
| Boc | Benzyloxycarbonyl |

BIOLOGICAL DATA

Biological data for compounds of the invention useful as MC4R agonists is set forth in Table 2. Biological data for compounds of the invention useful as MC1R agonists is set forth in Table 3.

Reporter Gene Assay

CHO-6×CRE-luc$^+$ reporter cell lines expressing human MC1R, MC3R, MC4R, and MC5R (GenBank accession numbers X65634, L06155, S77415 and U08353) and the CHO host reporter gene cell line were propagated in complete medium in T225 flasks. Forty-eight hours prior to assay, cells were harvested with 2 ml of 0.05% trypsin, washed with complete medium and plated at a concentration of 4000 cells/well in complete medium. Sixteen hours prior to the assay, the medium was removed from the cells and replaced with 90 μl/well of serum-free DMEM/F12. At the time of the assay the compounds were added in a 10 μl volume and plates were incubated for 4 h at 37° C. in a cell culture incubator. The medium was aspirated followed by the addition of 50 μl of a 1:1 mixture of LucLite™ and dPBS containing 1 mM $CaCl_2$ and 1 mM $MgCl_2$. The plates were then sealed and subjected to dark adaptation at room temperature for 10 min before luciferase activity was quantitated on a TopCount™ microplate scintillation counter (Packard) using 3 s/well count time. The NDP-αMSH and 154N-5 concentration-response curve data were expressed as a percentage of the fold stimulation in the NDP-αMSH control for each receptor subtype. The control value is the average of duplicate wells treated with 1×10$^{-7}$ M NDP-αMSH.

TABLE 2

Biological Data for Compounds Exhibiting MC4R Agonist Activity

| Example | pEC$_{50}$ | % Max MSH |
|---|---|---|
| 1 | 6.38 | 56 |
| 2 | 6.55 | 51 |
| 3 | 7.37 | 58 |
| 4 | 7.35 | 52 |
| 5 | 6.82 | 78 |
| 6 | 6.69 | 51 |
| 7 | 6.46 | 77 |
| 8 | 6.46 | 53 |
| 9 | 6.41 | 65 |
| 10 | 6.40 | 49 |
| 11 | 6.38 | 55 |
| 12 | 6.36 | 56 |
| 13 | 6.29 | 65 |

TABLE 3

Biological Data for Compounds Exhibiting MC1R Agonist Activity

| Example # | pEC$_{50}$ | % of MSH |
|---|---|---|
| 1 | 7.53 | 68 |
| 2 | 7.73 | 85 |
| 3 | 6.95 | 73 |
| 4 | 7.15 | 74 |
| 6 | 7.65 | 91 |
| 7 | 7.39 | 50 |
| 8 | 6.83 | 72 |
| 9 | 6.70 | 37 |
| 10 | 7.14 | 84 |
| 11 | 6.84 | 68 |
| 12 | 7.71 | 61 |
| 13 | 6.96 | 64 |
| 14 | 6.57 | 69 |
| 15 | 8.80 | 61 |
| 16 | 8.80 | 61 |
| 17 | 8.80 | 83 |
| 18 | 8.80 | 87 |
| 19 | 7.85 | 53 |
| 20 | 6.72 | 51 |
| 21 | 7.45 | 79 |

TABLE 3-continued
Biological Data for Compounds Exhibiting MC1R Agonist Activity
| Example # | pEC$_{50}$ | % of MSH |
|---|---|---|
| 22 | 7.30 | 54 |
| 23 | 7.29 | 72 |
| 24 | 8.80 | 86 |
| 25 | 7.19 | 72 |
| 26 | 7.13 | 41 |
| 27 | 6.89 | 95 |
| 28 | 6.80 | 79 |
| 29 | 6.74 | 103 |
| 30 | 6.69 | 69 |
| 31 | 6.65 | 40 |
| 32 | 6.53 | 54 |
What is claimed is:
1. A compound selected from the group consisting of
| Example # | Structure |
|---|---|
| 2 | 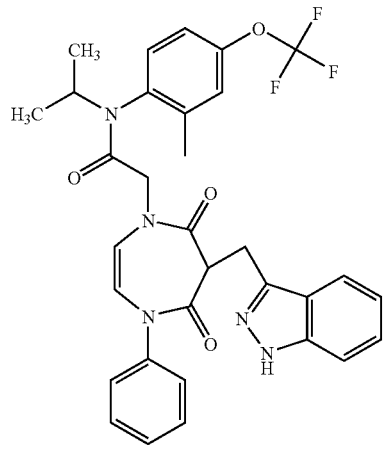 |
| 3 | 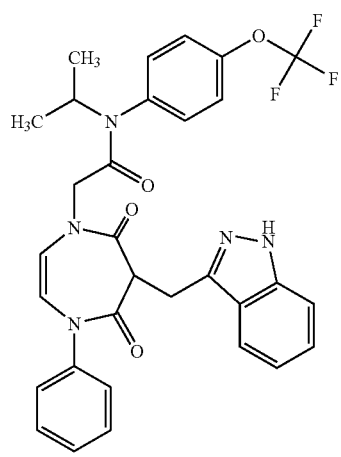 |
| 4 | (see structure above right) |
| 5 | 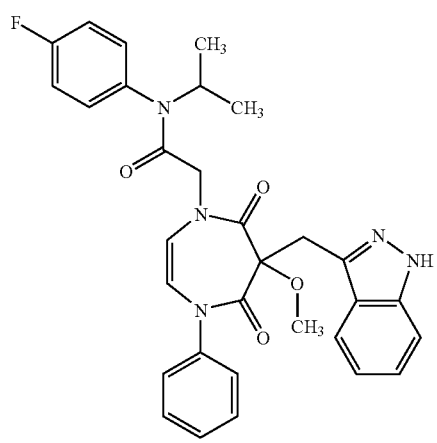 |
| 6 | (see structure below right) |

-continued
7
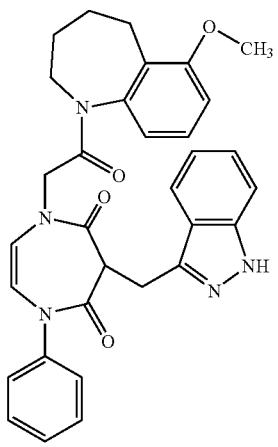
8
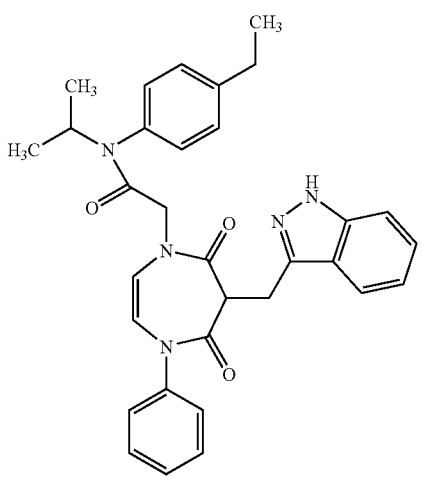
9
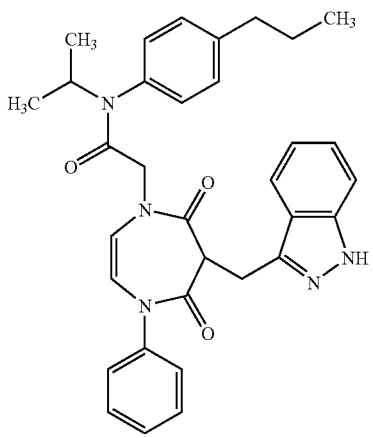
-continued
10
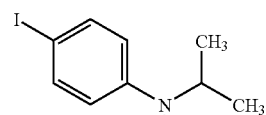
11
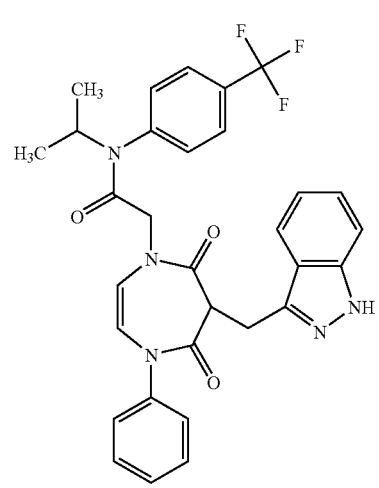
12
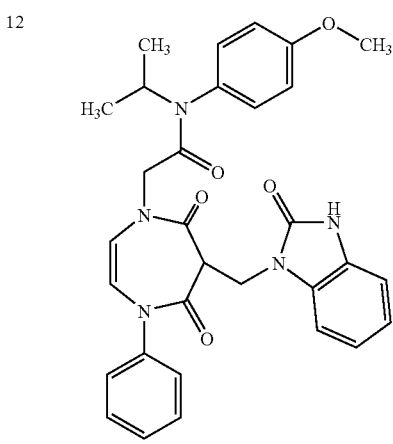

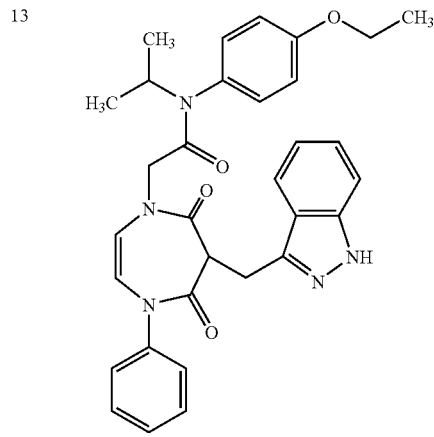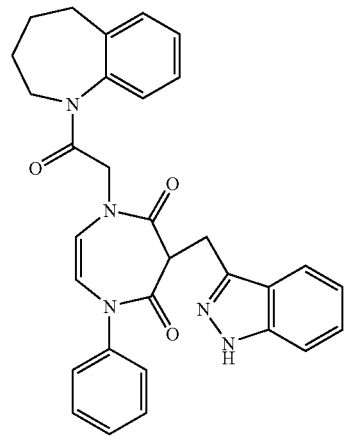

| 83 | 84 |
|---|---|
| 19 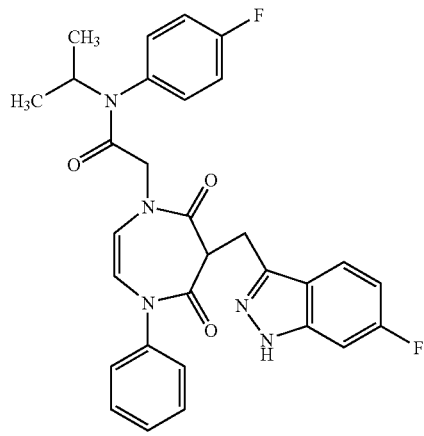 | 22 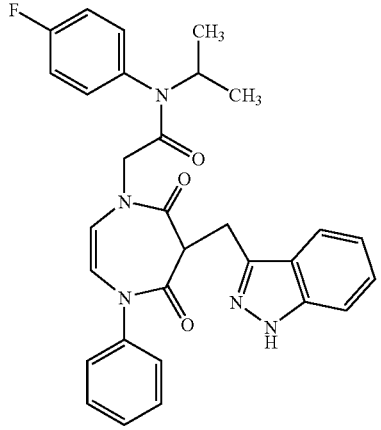 |
| 20 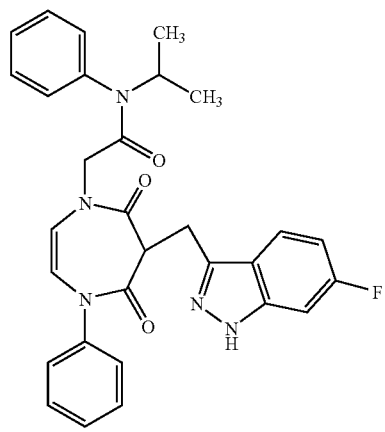 | 23 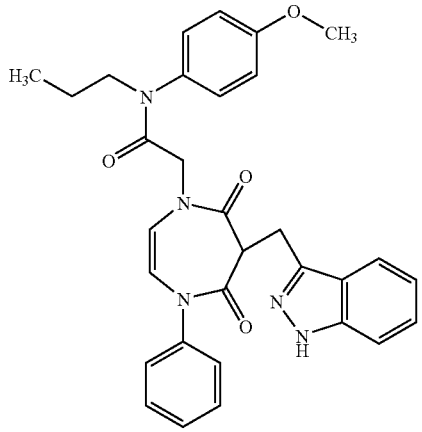 |
| 21 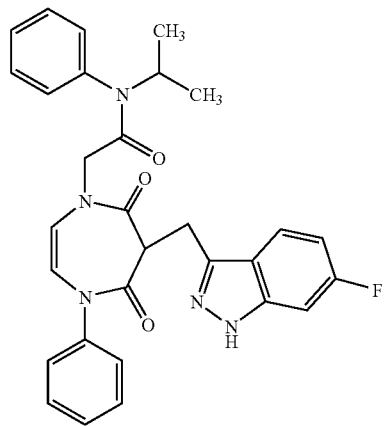 | 24 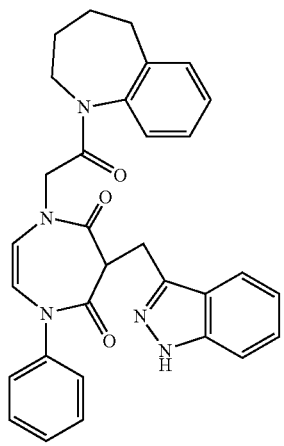 |

| 25 | 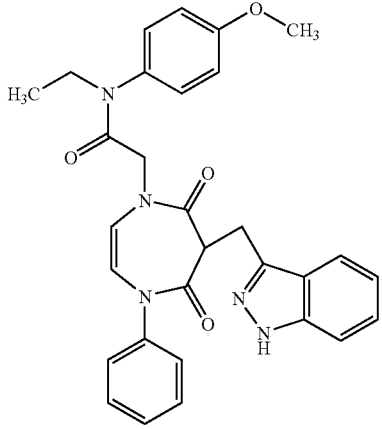 | 28 | 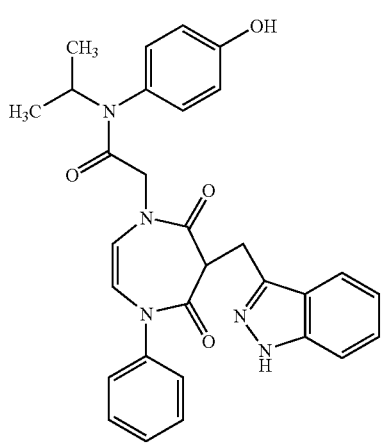 |
| 26 | 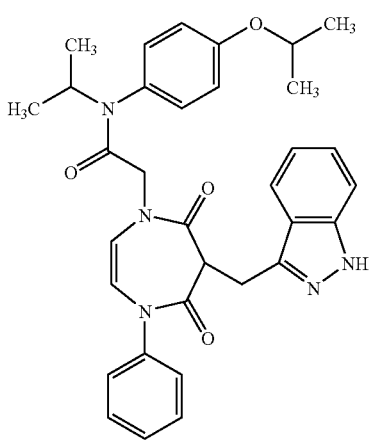 | 29 | 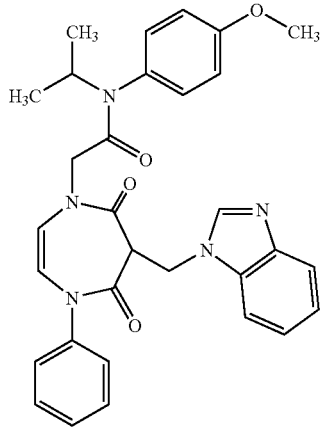 |
| 27 | 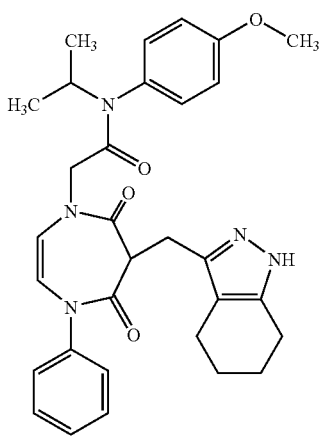 | 30 | 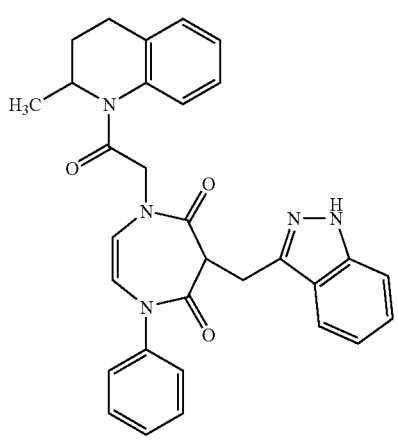 |

| | |
|---|---|
| 31 | 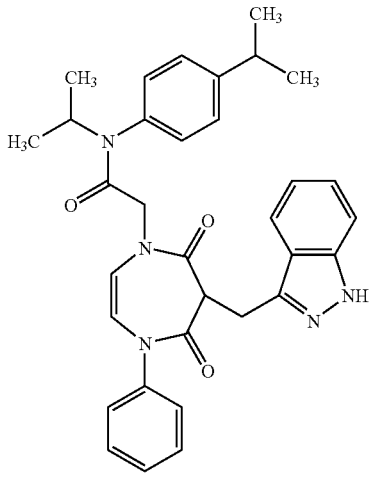 |
| 32 | 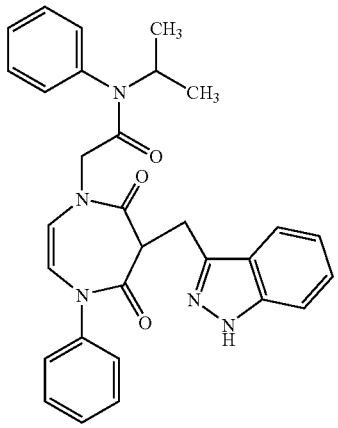 |

| Example # | Name |
|---|---|
| 2 | (Chiral) 2-[2,4-dioxo-3-(1H-indazol-3-ylmethylene)-5-phenyl-2,3,4,5-tetrahydro-1H-1,5-diazepin-1-yl]-N-isopropyl-N-(4-methoxyphenyl)acetamide |
| 3 | 2-[2,4-dioxo-3-(1H-indazol-3-ylmethylene)-5-phenyl-2,3,4,5-tetrahydro-1H-1,5-diazepin-1-yl]-N-(4-chlorophenyl)-N-isopropylacetamide |
| 4 | 2-[2,4-dioxo-3-(1H-indazol-3-ylmethylene)-5-phenyl-2,3,4,5-tetrahydro-1H-1,5-diazepin-1-yl]-N-isopropyl-N-(2-methyl-4-trifluoromethoxy)phenyl)acetamide |
| 5 | 2-[2,4-dioxo-3-(1H-indazol-3-ylmethylene)-3-methoxy-5-phenyl-2,3,4,5-tetrahydro-1H-1,5-diazepin-1-yl]-N-(4-fluorophenyl) N-isopropylacetamide |
| 6 | 2-[2,4-dioxo-3-(1H-indazol-3-ylmethylene)-5-phenyl-2,3,4,5-tetrahydro-1H-1,5-diazepin-1-yl]-N-isopropyl-N-(4-(trifluoromethoxyphenyl)acetamide |
| 7 | 3-(1H-indazol-3-ylmethylene)-1-[2-(6-methoxy-2,3,4,5-tetrahydro-1H-1-benzazepin-1-yl)-2-oxoethyl]-5-phenyl-1H-1,5-diazepine-2,4-dione |
| 8 | 2-[2,4-dioxo-3-(1H-indazol-3-ylmethylene)-5-phenyl-2,3,4,5-tetrahydro-1H-1,5-diazepin-1-yl]-N-(4-ethylphenyl)-N-isopropylacetamide |
| 9 | 2-[2,4-dioxo-3-(1H-indazol-3-ylmethylene)-5-phenyl-2,3,4,5-tetrahydro-1H-1,5-diazepin-1-yl]-N-isopropyl-N-(4-propylphenyl)acetamide |
| 10 | 2-[2,4-dioxo-3-(1H-indazol-3-ylmethylene)-5-phenyl-2,3,4,5-tetrahydro-1H-1,5-diazepin-1-yl]-N-(4-iodophenyl)-N-isopropylacetamide |
| 11 | 2-[2,4-dioxo-3-(1H-indazol-3-ylmethylene)-5-phenyl-2,3,4,5-tetrahydro-1H-1,5-diazepin-1-yl]-N-isopropyl-N-(4-trifluoromethylphenyl)acetamide |
| 12 | 2-[2,4-dioxo-3-(2,3-dihydro-2-oxo-1H-benzimidazol-1-yl)-methylene-5-phenyl-2,3,4,5-tetrahydro-1H-1,5-diazepin-1-yl]-N-isopropyl-N-(4-methoxyphenyl)acetamide |
| 13 | 2-[2,4-dioxo-3-(1H-indazol-3-ylmethylene)-5-phenyl-2,3,4,5-tetrahydro-1H-1,5-diazepin-1-yl]-N-(4-ethoxyphenyl)-N-isopropylacetamide |
| 14 | 2-[2,4-dioxo-3-(1H-indazol-3-ylmethylene)-5-phenyl-2,3,4,5-tetrahydro-1H-1,5-diazepin-1-yl]-N-isopropyl-N-(4-methylphenyl)acetamide |
| 15 | 3-(6-fluoro-1H-indazol-3-ylmethylene)-1-[2-oxoethyl-2-(2,3,4,5-tetrahydro-1H-1-benzazepin-1-yl)]-5-phenyl-1H-1,5-diazepine-2,4-dione |
| 16 | 3-(1H-indazol-3-ylmethylene)-1-[2-oxoethyl-2-(2,3,4,5-tetrahydro-1H-1-benzazepin-1-yl)]-5-phenyl-1H-1,5-diazepine-2,4-dione |
| 17 | 2-[2,4-dioxo-3-(6-fluoro-1H-indazol-3-ylmethylene)-5-phenyl-2,3,4,5-tetrahydro-1H-1,5-diazepin-1-yl]-N-isopropyl-N-(4-methoxyphenyl)acetamide |
| 18 | (Chiral) 3-(1H-indazol-3-ylmethylene)-1-[2-oxoethyl-2-(2,3,4,5-tetrahydro-1H-1-benzazepin-1-yl)]-5-phenyl-1H-1,5-diazepine-2,4-dione |
| 19 | 2-[2,4-dioxo-3-(6-fluoro-1H-indazol-3-ylmethylene)-5-phenyl-2,3,4,5-tetrahydro-1H-1,5-diazepin-1-yl]-N-(4-fluorophenyl)-N-isopropylacetamide |
| 20 | 2-[2,4-dioxo-3-(6-fluoro-1H-indazol-3-ylmethylene)-5-phenyl-2,3,4,5-tetrahydro-1H-1,5-diazepin-1-yl]-N-isopropyl-N-phenylacetamide |
| 21 | (Chiral) 2-[2,4-dioxo-3-(6-fluoro-1H-indazol-3-ylmethylene)-5-phenyl-2,3,4,5-tetrahydro-1H-1,5-diazepin-1-yl]-N-isopropyl-N-phenylacetamide |
| 22 | 2-[2,4-dioxo-3-(1H-indazol-3-ylmethylene)-5-phenyl-2,3,4,5-tetrahydro-1H-1,5-diazepin-1-yl]-N-(4-fluorophenyl)-N-isopropylacetamide |
| 23 | 2-[2,4-dioxo-3-(1H-indazol-3-ylmethylene)-5-phenyl-2,3,4,5-tetrahydro-1H-1,5-diazepin-1-yl]-N-(4-methoxyphenyl)-N-propylacetamide |
| 24 | (Chiral) 3-(1H-indazol-3-ylmethylene)-1-[2-oxoethyl-2-(2,3,4,5-tetrahydro-1H-1-benzazepin-1-yl)]-5-phenyl-1H-1,5-diazepine-2,4-dione |
| 25 | 2-[2,4-dioxo-3-(1H-indazol-3-ylmethylene)-5-phenyl-2,3,4,5-tetrahydro-1H-1,5-diazepin-1-yl]-N-ethyl-N-(4-methoxyphenyl)acetamide |
| 26 | 2-[2,4-dioxo-3-(1H-indazol-3-ylmethylene)-5-phenyl-2,3,4,5-tetrahydro-1H-1,5-diazepin-1-yl]-N-(4-isopropoxyphenyl)-N-isopropylacetamide |
| 27 | 2-[2,4-dioxo-5-phenyl-3-(4,5,6,7-tetrahydro-1H-indazol-3-ylmethylene)-2,3,4,5-tetrahydro-1H-1,5-diazepin-1-yl]-N-isopropyl-N-(4-methoxyphenyl)acetamide |
| 28 | (Chiral) 2-[2,4-dioxo-3-(1H-indazol-3-ylmethylene)-5-phenyl-2,3,4,5-tetrahydro-1H-1,5-diazepin-1-yl]-N-(4-hydroxyphenyl)-N-isopropylacetamide |
| 29 | 2-[2,4-dioxo-3-(1H-benzimidazol-1-ylmethylene)-5-phenyl-2,3,4,5-tetrahydro-1H-1,5-diazepin-1-yl]-N-isopropyl-N-(4-methoxyphenyl)acetamide |
| 30 | 1-[2-(3,4-dihydro-2H-2-methylquinolin-1-yl)-2-oxoethyl]-3-(1H-indazol-3-ylmethylene)-5-phenyl-1H-1,5-diazepine-2,4-dione |
| 31 | 2-[2,4-dioxo-3-(1H-indazol-3-ylmethylene)-5-phenyl-2,3,4,5-tetrahydro-1H-1,5-diazepin-1-yl]-N-isopropyl-N-(4-isopropylphenyl)acetamide |

| | |
|---|---|
| 32 | (Chiral) 2-[2,4-dioxo-3-(1H-indazol-3-ylmethylene)-5-phenyl-2,3,4,5-tetrahydro-1H-1,5-diazepin-1-yl]-N-isopropyl-N-phenylacetamide | and salts thereof.

2. A pharmaceutical composition comprising a compound of claim 1, or a physiologically acceptable salt thereof and one or more pharmaceutically acceptable carriers, diluents and excipients.

3. A method for treating obesity, which method comprises the administration to a mammal, including a human, of a therapeutically effective amount of a compound of claim 1, or a salt thereof.

* * * * *